(12) United States Patent
Lee et al.

(10) Patent No.: US 11,890,107 B2
(45) Date of Patent: *Feb. 6, 2024

(54) SYSTEMS AND METHODS FOR MONITORING A PATIENT

(71) Applicant: The Regents of the University of California, Oakland, CA (US)

(72) Inventors: Hanmin Lee, San Francisco, CA (US); Sachin Rangarajan, San Francisco, CA (US); Isabelle Chumfong, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 17/245,643

(22) Filed: Apr. 30, 2021

(65) Prior Publication Data

US 2021/0330246 A1    Oct. 28, 2021

Related U.S. Application Data

(63) Continuation of application No. 16/068,847, filed as application No. PCT/US2017/013235 on Jan. 12, 2017, now Pat. No. 11,020,046.
(Continued)

(51) Int. Cl.
*A61B 5/00* (2006.01)
*A61B 5/11* (2006.01)
*G16H 50/20* (2018.01)

(52) U.S. Cl.
CPC ............ *A61B 5/447* (2013.01); *A61B 5/0004* (2013.01); *A61B 5/0022* (2013.01);
(Continued)

(58) Field of Classification Search
CPC ..... A61B 5/447; A61B 5/0004; A61B 5/0022; A61B 5/1115; A61B 5/4848;
(Continued)

(56) References Cited

U.S. PATENT DOCUMENTS 4,554,930 A * 11/1985 Kress ...................... A61B 5/447
600/587
5,153,040 A    10/1992 Faasse, Jr.
(Continued)

FOREIGN PATENT DOCUMENTS

WO    2015003211    1/2015

*Primary Examiner* — May A Abouelela
(74) *Attorney, Agent, or Firm* — Edward J. Baba; Bozicevic, Field & Francis LLP

(57) ABSTRACT

Provided herein are methods and systems for monitoring a patient using a pressure-sensing device containing a pressure-sensitive region configured to selectively overlie a pressure ulcer-prone body part of the patient. In some embodiments, the pressure-sensing device includes a multilayered sensing unit containing a pressure-sensing layer to sense force and an adhesive layer configured to attach the pressure-sensing device to the body part. Also provided is a kit that includes the pressure-sensing device. The present methods, systems, and kits may find use in reducing the risk of pressure ulcer development in a patient.

17 Claims, 28 Drawing Sheets

Related U.S. Application Data

(60) Provisional application No. 62/279,213, filed on Jan. 15, 2016.

(52) U.S. Cl.
CPC .......... *A61B 5/1115* (2013.01); *A61B 5/4848* (2013.01); *A61B 5/6833* (2013.01); *A61B 5/6892* (2013.01); *A61B 5/7225* (2013.01); *A61B 5/7242* (2013.01); *A61B 5/7275* (2013.01); *A61B 5/742* (2013.01); *A61B 5/7405* (2013.01); *A61B 5/746* (2013.01); *A61B 5/7455* (2013.01); *G16H 50/20* (2018.01); *A61B 2562/0247* (2013.01); *A61B 2562/046* (2013.01)

(58) Field of Classification Search
CPC ... A61B 5/6833; A61B 5/6892; A61B 5/7225; A61B 5/7242; A61B 5/7275; A61B 5/7405; A61B 5/742; A61B 5/7455; A61B 5/746; A61B 2562/0247; A61B 2562/046; G16H 50/20
See application file for complete search history.

(56) References Cited

U.S. PATENT DOCUMENTS

| | | | | |
|---|---|---|---|---|
| 5,253,656 A * | 10/1993 | Rincoe | ............... | A61F 2/76 600/595 |
| 5,540,922 A | 7/1996 | Fabo | | |
| 5,755,681 A | 5/1998 | Plews | | |
| 6,014,346 A * | 1/2000 | Malone | ............... | G04F 1/005 600/595 |
| 6,030,351 A * | 2/2000 | Schmidt | ............... | A61B 5/6887 600/595 |
| 6,287,253 B1 * | 9/2001 | Ortega | ............... | A61B 5/002 600/300 |
| 6,918,883 B2 * | 7/2005 | Horton | ............... | A61B 5/1036 600/592 |
| 6,987,232 B2 * | 1/2006 | Smith | ............... | A61B 5/6892 340/573.5 |
| 7,094,944 B2 | 8/2006 | Faasse, Jr. | | |
| 8,161,826 B1 * | 4/2012 | Taylor | ............... | A47C 27/082 73/862.041 |
| 8,497,407 B2 | 7/2013 | Fabo et al. | | |
| 8,672,842 B2 * | 3/2014 | Kenalty | ............... | A61B 5/0015 600/587 |
| 2004/0078219 A1 * | 4/2004 | Kaylor | ............... | G16H 40/67 600/300 |
| 2004/0126413 A1 | 7/2004 | Sigurjonsson et al. | | |
| 2005/0165284 A1 * | 7/2005 | Gefen | ............... | A61B 5/103 600/557 |
| 2006/0065060 A1 * | 3/2006 | Ito | ............... | G01D 7/00 73/862.046 |
| 2009/0070939 A1 * | 3/2009 | Hann | ............... | A61B 5/447 5/652.1 |
| 2010/0101022 A1 * | 4/2010 | Riley | ............... | A61B 5/024 702/19 |
| 2010/0268122 A1 * | 10/2010 | Drennan | ............... | A61B 5/103 600/587 |
| 2011/0015498 A1 * | 1/2011 | Mestrovic | ............... | A61B 5/6807 600/592 |
| 2012/0053423 A1 * | 3/2012 | Kenalty | ............... | A61B 5/6892 600/300 |
| 2012/0053424 A1 * | 3/2012 | Kenalty | ............... | A61B 5/0205 600/300 |
| 2012/0065547 A1 * | 3/2012 | Hann | ............... | A61B 5/11 600/587 |
| 2012/0109013 A1 * | 5/2012 | Everett | ............... | A61B 5/1038 600/587 |
| 2012/0190989 A1 * | 7/2012 | Kaiser | ............... | A61B 5/08 600/300 |
| 2012/0259248 A1 * | 10/2012 | Receveur | ............... | A61G 7/0514 600/595 |
| 2012/0283979 A1 * | 11/2012 | Bruekers | ............... | A61B 5/01 702/141 |
| 2013/0006151 A1 * | 1/2013 | Main | ............... | A61G 7/057 600/587 |
| 2013/0090571 A1 * | 4/2013 | Nourani | ............... | G16H 20/30 600/587 |
| 2013/0317393 A1 * | 11/2013 | Weiss | ............... | A61B 5/447 600/587 |
| 2014/0039351 A1 | 2/2014 | Mix et al. | | |
| 2014/0135657 A1 | 5/2014 | Wu et al. | | |
| 2014/0296749 A1 * | 10/2014 | Reid, Jr. | ............... | A61F 13/085 600/587 |
| 2014/0343889 A1 * | 11/2014 | Ben Shalom | ............... | A61B 5/1117 600/595 |
| 2014/0350882 A1 | 11/2014 | Everett et al. | | |
| 2015/0257711 A1 * | 9/2015 | Chen | ............... | A61B 5/1126 601/134 |
| 2015/0297132 A1 * | 10/2015 | Bichel | ............... | A61B 5/1116 600/595 |
| 2015/0320352 A1 * | 11/2015 | Ben Shalom | ............... | A61B 5/6892 600/587 |
| 2019/0021650 A1 * | 1/2019 | Lee | ............... | A61B 5/6892 |

* cited by examiner

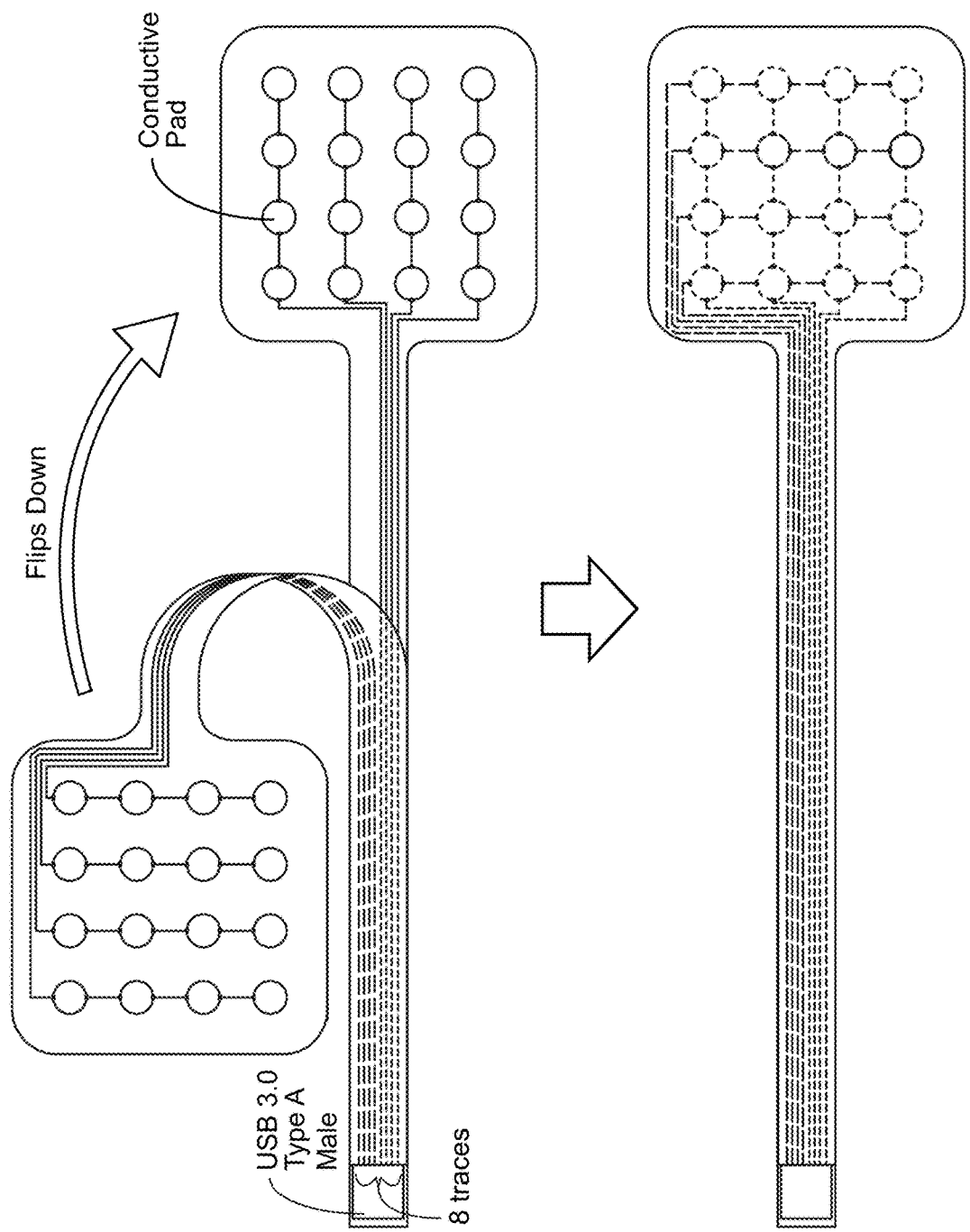

| Column | USB Pin # |
|--------|-----------|
| 1 | 1 |
| 2 | 8 |
| 3 | 2 |
| 4 | 7 |

FIG. 11
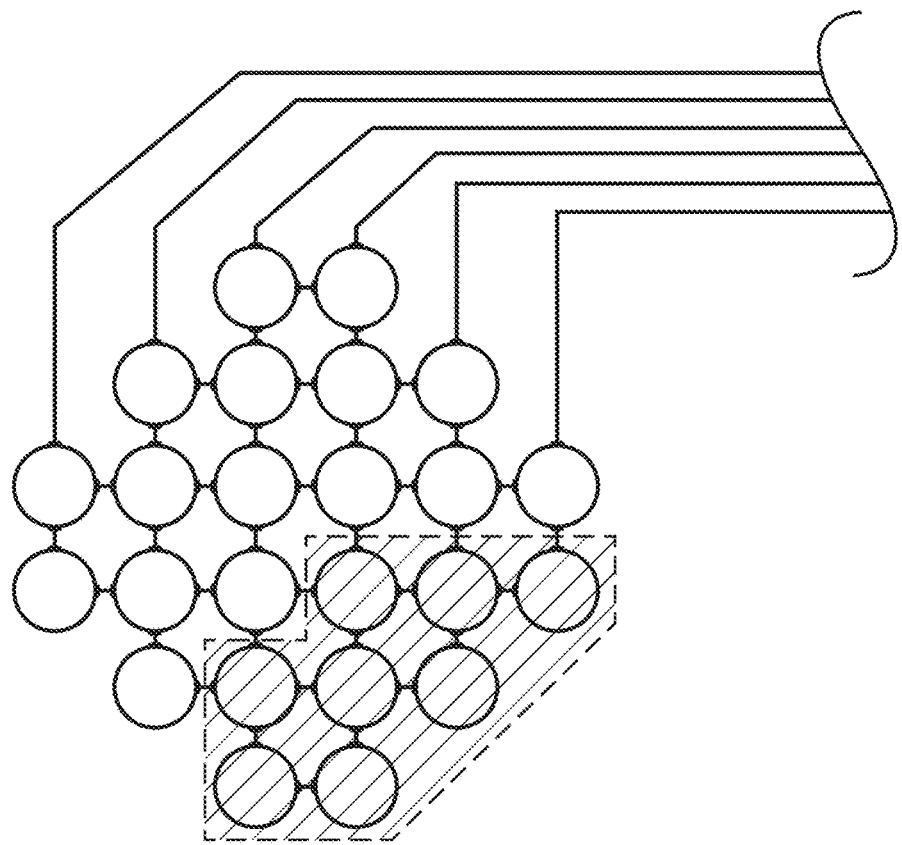
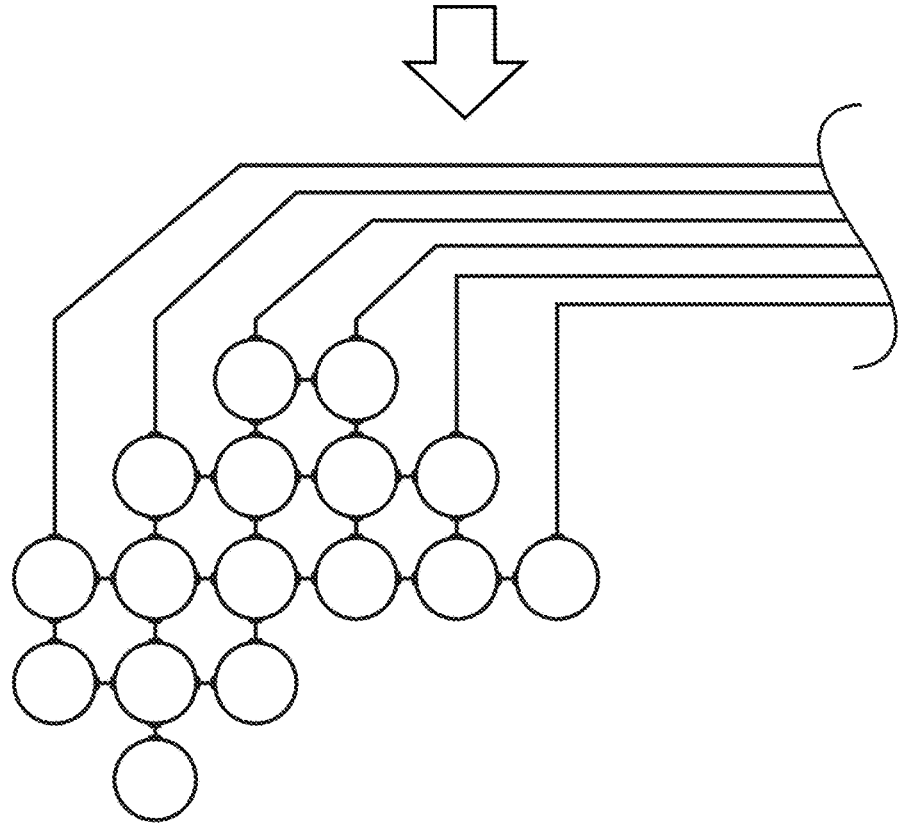

FIG. 12
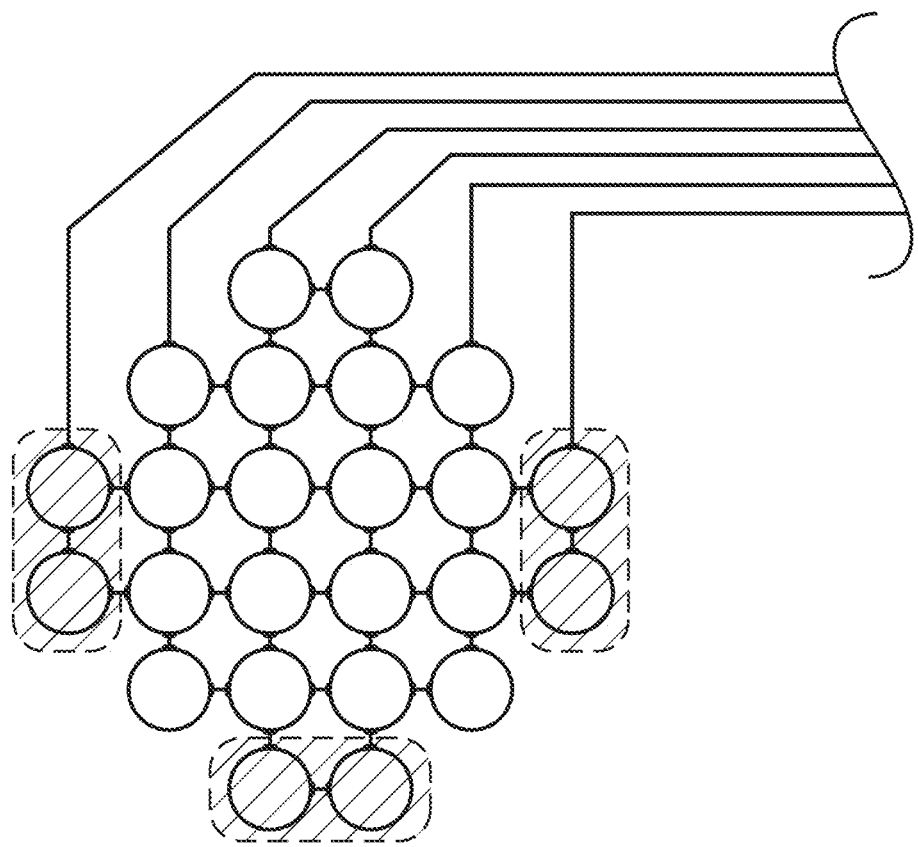
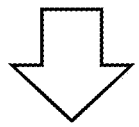
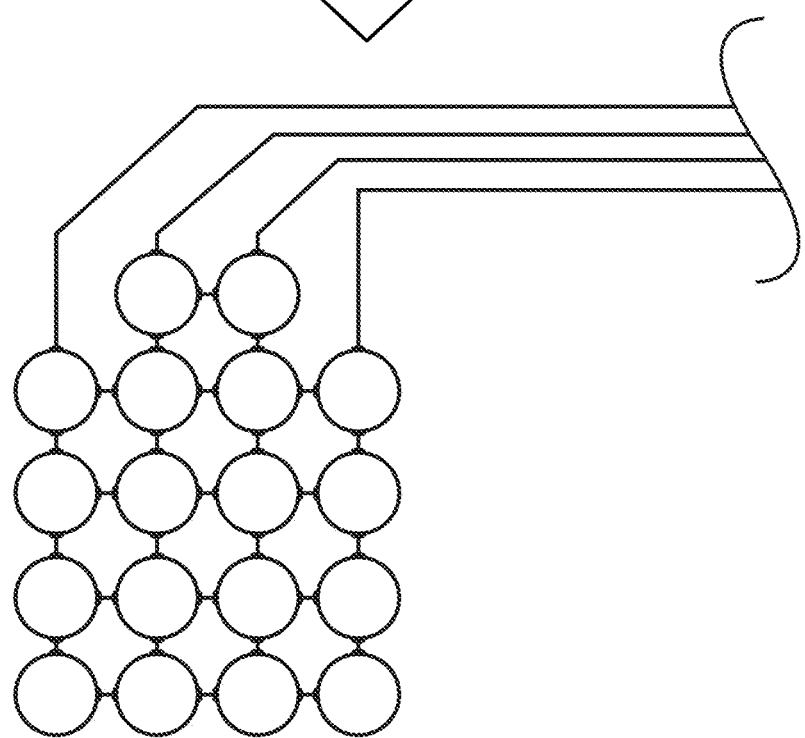

SYSTEMS AND METHODS FOR MONITORING A PATIENT

CROSS-REFERENCE TO RELATED APPLICATIONS

This application is a continuation of U.S. patent application Ser. No. 16/068,847, filed on Jul. 9, 2018, issued as U.S. Pat. No. 11,020,046, which is a 371 of PCT/US2017/013235, filed on Jan. 12, 2017, which claims priority to U.S. Provisional Patent Application Ser. No. 62/279,213, filed on Jan. 15, 2016, the disclosures of which are herein incorporated by reference in their entirety.

STATEMENT REGARDING FEDERALLY SPONSORED RESEARCH

This invention was made with government support under grant no. 1240380 awarded by the National Science Foundation. The government has certain rights in the invention.

BACKGROUND

Each year, pressure ulcers (also known as decubitus ulcers) occur in an estimated 2.5 million Americans, and may lead to 60,000 deaths, at an annual cost of $11-30 billion to the U.S. health system. Pressure ulcers are considered a serious but preventable patient safety error, occurring in hospitals, nursing facilities, rehabilitation facilities and private homes. Pressure ulcers may develop in patients who are immobile, when the skin and subcutaneous tissues are compressed between the bed and a bony prominence. Prolonged pressure on the tissues may lead to tissue necrosis. Later-stage pressure ulcers are associated with high morbidity, mortality and cost.

SUMMARY

Provided herein are methods and systems for monitoring a patient using one or more pressure-sensing devices. The pressure-sensing device may contain a pressure-sensitive region configured to selectively overlie a pressure ulcer-prone body part of the patient. In some embodiments, the pressure-sensing device includes a multilayered sensing unit containing a pressure-sensing layer to sense force and an adhesive layer configured to attach the pressure sensing device to the body part.

A method of the present disclosure may include a) obtaining data from a pressure-sensing device having a pressure-sensitive region that selectively overlies a pressure ulcer-prone body part of a body of a patient, wherein the pressure-sensing device is configured to sense force applied to the body part and generate data containing a pressure measurement, $p_t$, based on the force sensed at time t; b) analyzing the data using one or more threshold criteria, each of the one or more threshold criteria including a threshold value, to determine whether the one or more threshold criteria have been met; and c) generating an output that indicates whether the one or more threshold criteria are met. In some embodiments, the pressure-sensing device contains a multilayered sensing unit including: a pressure-sensing layer containing an array of interconnected pressure-sensitive elements, wherein each pressure-sensitive element of the array is configured to sense the force applied to the body part and generate a signal representative of a magnitude of the force; and an adhesive layer configured to attach the pressure-sensing device to the body part. In some embodiments, the array is an array containing one or more rows and one or more columns of pressure-sensitive elements. In some embodiments, a location within the grid of each of the pressure-sensitive elements is specified by a row number and a column number. In some embodiments, the data contains information for a grid coordinate of the pressure-sensitive element from which the signal originated.

In any embodiment, the data may contain real-time measurements of pressure applied to the body part.

In any embodiment, the analyzing may include calculating: a time-differential of the pressure measurements:

$$\frac{dP(t)}{dt},$$

where P(t) is a function including a temporal sequence of the pressure measurements value, $p_t$; and/or a time-integral of the pressure measurements: $\int_0^{t_0} P(t)dt$, wherein $t_0$ is the time of a current pressure measurement.

In any embodiment, the output may include an auditory output, a visual output, and/or a tactile output. In some embodiments, the output is a tiered output including a plurality of tiers of output, wherein the tier of the output is based on the whether the one or more threshold criteria are met. In some embodiments, the tiered output includes a high-, intermediate- and low-tier outputs, wherein a first net number of criteria met to generate a high-tier output is higher than a second net number of criteria met to generate an intermediate-tier output, and the second net number of criteria met is higher than a third net number of criteria met to generate a low-tier output. In some embodiments, the output is a color-coded visual output.

In any embodiment, the data may contain a pressure measurement, $p_{n,t}$, at time t, wherein n is a patient identifier, and wherein the one or more threshold criteria are one or more patient-specific criteria, each of the patient-specific criteria including one of one or more patient-specific threshold values. In some embodiments, the one or more patient-specific threshold values includes a threshold pressure value, $\kappa_n$, a threshold first time derivative of pressure, $\kappa'_n$, a threshold second time derivative of pressure, $\kappa''_n$, and/or one or more threshold time integrals of pressure, $K_{n,x}$, where x is an integer, for patient n. In some embodiments, the one or more patient-specific criteria are based on patient-specific risk-factors for pressure ulcer development. In some embodiments, the risk-factors for pressure ulcer development include one or more of age, immobility, diabetes, peripheral vascular disease (PVD), cardiac failure, kidney failure, neurological disorder, malnutrition, sepsis, incontinence, spinal cord injury, anemia, skin condition, prolonged surgery, weight loss, obesity, time since admission, type of admission, albumin, prealbumin, CRP, creatinine, glucose, sodium, potassium, bicarbonate, blood urea nitrogen, white blood cell count, hematocrit, platelet count, total bilirubin, pH, pCO2, pO2, FiO2, hemoglobin A1c, urine output, history of acute renal failure, history of paralytic drug use, days of paralytic drug use, history of vasoactive drug use, days of vasoactive drug use, heart rate, mean arterial pressure, systolic blood pressure, diastolic blood pressure, respiration rate, oxygenation, temperature (max/min), Glasgow Coma Score, history of mechanical ventilation or other positive pressure ventilation, days of ventilator use, history of incontinence, days of incontinence, history of metastatic cancer, history of hematologic malignancy, history of AIDS, history of severe organ system insufficiency or immunocompromised status, and history of spinal cord injury leading to paresis or paralysis.

In some embodiments, the patient-specific threshold criterion includes a pressure threshold value, $\kappa_n$, and wherein the analyzing includes: b-i) determining that the patient-specific threshold criterion is met when $p_{n,t} \geq \kappa_n$, and determining that the one or more patient-specific criteria are not met when $p_{n,t} < \kappa_n$. In some embodiments, the patient-specific threshold criterion includes a patient-specific threshold first time derivative of pressure, $\kappa'_n$, and wherein the analyzing includes: b-ii) determining that the one or more patient-specific criteria are met when $$\frac{dP_n(t)}{dt} \geq \kappa'_n$$

at $t=t_0$, Where $P_n(t)$ is a function containing a sequence of pressure measurements, $p_{n,t}$, for patient n, and $t_0$ is the time of a current pressure measurement. In some embodiments, the determining step b-ii) further includes: determining that no patient-specific criteria are met when $$\frac{dP_n(t)}{dt} < \kappa'_n$$

at $t=t_0$. In some embodiments, the determining step b-ii) further includes, when $$\frac{dP_n(t)}{dt} < \kappa'_n$$

at $t=t_0$: determining that one or more patient-specific criteria are met when $$\frac{dP_n(t)}{dt} \geq 0$$

for all t, where $t_0 < t < t_0+T_{n,1}$, where $T_{n,1}$ is a patient-specific, first monitoring time; or determining that no patient-specific criteria are met when $$\frac{dP_n(t)}{dt} < 0$$

for some t, where $t_0 < t < t_0+T_{n,1}$. In some embodiments, the patient-specific threshold criterion includes a patient-specific threshold second time derivative of pressure, $\kappa''_n$, and wherein the determining step b-ii) further includes, when $$\frac{dP_n(t)}{dt} \geq \kappa'_n$$

at $t=t_0$: determining that one or more patient-specific criteria are met when $$\frac{d^2P_n(t)}{dt^2} \geq \kappa''_n$$

at $t=t_0$; determining that one or more patient-specific criteria are met when $$\frac{d^2P_n(t)}{dt^2} < \kappa''_n$$

at $t=t_0$, and $$\frac{d^2P_n(t)}{dt^2} \geq 0$$

for all t, where $t_0 < t < t_0+T_{n,2}$, where $T_{n,2}$ is a patient-specific, second monitoring time; or determining that no patient-specific criteria are met when $$\frac{d^2P_n(t)}{dt^2} < \kappa''_n$$

at $t=t_0$, and $$\frac{d^2P_n(t)}{dt^2} < 0$$

for some t, where $t_0 < t < t_0+T_{n,2}$. In some embodiments, the generating step c) includes: c-i) when $$\frac{dP_n(t)}{dt} < \kappa'_n$$

at $t=t_0$: generating an intermediate-tier output of a tiered output when $$\frac{dP_n(t)}{dt} \geq 0$$

for all t, where $t_0 < t < t_0+T_{n,1}$; and generating a low-tier output of the tiered output when $$\frac{dP_n(t)}{dt} \leq 0$$

for some t, where $t_0 < t < t_0+T_{n,1}$; or c-ii) when $$\frac{dP_n(t)}{dt} \geq \kappa'_n$$

at $t=t_0$: generating a high-tier output of the tiered output when $$\frac{d^2P_n(t)}{dt^2} \geq \kappa''_n$$

at $t=t_0$, or when $$\frac{d^2 P_n(t)}{dt^2} < \kappa''_n,$$

at $t=t_0$, and $$\frac{d^2 P_n(t)}{dt^2} \geq 0$$

for all t, where $t_0 < t < t_0 + T_{n,2}$; and generating an intermediate-tier output of the tiered output when $$\frac{d^2 P_n(t)}{dt^2} < \kappa''_n,$$

at $t=t_0$, and $$\frac{d^2 P_n(t)}{dt^2} < 0$$

for some t, where $t_0 < t < t_0 + T_{n,2}$. In some embodiments, the one or more patient-specific threshold values include a first and second threshold time integrals of pressure, $K_{n,1}$ and $K_{n,2}$, respectively, and wherein the analyzing further comprises: b-iii) determining that one or more patient-specific criteria are met when: $\int_0^{t_0} P_n(t)dt \geq K_{n,1}$, or $\int_0^{t_0} P_n(t)dt < K_{n,1}$ and $\int_0^{t_0} P_n(t)dt \geq K_{n,2}$, wherein $K_{n,1} > K_{n,2}$, wherein $P_n(t)$ is a function containing a sequence of pressure measurements $p_{n,t}$, for patient n, and $t_0$ is the time of a current pressure measurement; and determining that no patient-specific threshold criterion is met when $\int_0^{t_0} P_n(t)dt < K_{n,1}$, and $\int_0^{t_0} P_n(t)dt < K_{n,2}$. In some embodiments, the patient is a repositioned patient, and the analyzing further comprises analyzing an effect of repositioning of the patient on the pressure measurement. In some embodiments, the repositioning of the patient begins at $t_{rep1}$ and ends at $t_{rep2}$, and wherein the one or more patient-specific threshold values further include a third threshold time integral of pressure, $K_{n,3}$, and wherein the generating further includes: c-iii) when $\int_0^{t_0} P_n(t)dt \geq K_{n,1}$: generating a high-tier output of a tiered output when $\int_0^{t_0} P_n(t)dt - \int_{t_{rep1}}^{t_{rep2}} (p_{n,t_{rep1}} - R_n(t)) \geq K_{n,3}$, wherein $p_{n,t_{rep1}}$ is the pressure measurement at the beginning of the repositioning of patient n, and $R_n(t)$ is a subset of $P_n(t)$ where $t_{rep1} \leq t \leq t_{rep2}$; and generating an intermediate-tier output of the tiered output when $\int_0^{t_0} P_n(t)dt - \int_{t_{rep1}}^{t_{rep2}} (p_{n,t_{rep1}} - R_n(t)) < K_{n,3}$; or c-iv) when $\int_0^{t_0} P_n(t)dt < K_{n,1}$: generating an intermediate-tier output of the tiered output when $\int_0^{t_0} P_n(t)dt \geq K_{n,2}$; and generating a low-tier output of the tiered output when $\int_0^{t_0} P_n(t)dt < K_{n,2}$.

In any embodiment, the method may further include: d) providing one or more instructions related to positioning of the patient's body, based on the one or more patient-specific criteria that are met and/or based on the generated output. In some embodiments, the one or more instructions include instructions to: continue monitoring the patient; turn the patient's body now; turn the patient's body within a predetermined amount of time; provide a level of intervention other than repositioning the patient; and/or seek medical attention.

In any embodiment, the method may include obtaining data from two or more pressure-sensing devices, each containing a pressure-sensitive region, wherein the pressure-sensitive regions overlie different pressure ulcer-prone body parts of the patient's body. In some embodiments, at least some of the pressure-sensitive regions of the one or more pressure-sensing devices overlie regions of the patient's body in a substantially symmetrical pattern across a line of symmetry. In some embodiments, the line of symmetry is the sagittal midline of the patient's body. In some embodiments, the analyzing further comprises analyzing the data from the two or more pressure-sensing devices, thereby determining whether the one or more threshold criteria have been met for each of the two or more pressure-sensing devices.

In any embodiment, the pressure-sensitive region of the pressure-sensing device may overlie a surface area of each of the body parts in the range of 1.0 to 10,000 cm².

In any embodiment, the patient may be a substantially immobile patient.

In any embodiment, the ulcer-prone body parts may include the occiput, upper back, lower back, elbow, hip, ischium, buttock, knee and/or the heel.

In any embodiment, the method may further include attaching the pressure-sensing device to the body of the patient in a manner sufficient to selectively overlay the pressure ulcer-prone body part with the pressure-sensitive region of the pressure-sensing device.

Also provided herein is a method of reducing the risk of a patient developing a pressure ulcer, including: monitoring a patient using an embodiment of a method of monitoring a patient, as described herein, thereby generating an output that indicates whether one or more threshold criteria are met; and repositioning the patient based on the output. In some embodiments, the repositioning the patient based on the output includes repositioning the patient within a predetermined time period when the one or more threshold criteria are met.

Also provided herein is a system for a user to monitor a patient, including: a) one or more pressure-sensing devices, wherein each of the pressure-sensing devices comprises a pressure-sensitive region configure to: be overlaid on one of one or more pressure ulcer-prone body parts of a body of a patient; and sense force applied to the body part, and wherein each of the pressure-sensing devices is configured to generate data containing a pressure measurement based on the sensed force; b) a controller including a communication unit configured to transmit the data generated by the one or more pressure-sensing devices; c) a computational unit containing: a processor; and a non-transient computer-readable memory containing instructions that, when executed by the processor, causes the computational unit to: i) obtain the data transmitted by the one or more pressure-sensing devices; and ii) analyze the obtained data using one or more threshold criteria, each of the one or more threshold criteria comprising a threshold value, to determine whether the one or more threshold criteria have been met; and d) a user-interface unit comprising an output unit configured to display an output containing: the transmitted data, or a processed form thereof; and/or an indication of whether the one or more threshold criteria are met by the analyzed data. In some embodiments, each of the pressure-sensing devices contains a multilayered sensing unit including: a pressure-sensing layer including an array of interconnected pressure-sensitive elements, wherein each pressure-sensitive element of the array is configured to sense the force applied to the body part and generate a signal representative of a magnitude of the force; and an adhesive layer configured to attach the pressure-sensing device to the body part. In some embodiments, the pressure-sensing layer comprises a first conductive layer comprising a first substrate, a second conductive layer contains a second substrate, and a piezoresistive layer containing a pressure-sensitive polymer, wherein the piezoresistive layer is interposed between the first and second conductive layers. In some embodiments, the pressure-sensitive elements each includes a conductive element disposed in each of the first conductive layer and the second conductive layer, wherein the conductive elements are in contact with the piezoresistive layer. In some embodiments, the pressure-sensitive polymer includes a piezoresistive polymer. In some embodiments, the array is a grid containing one or more rows and one or more columns of pressure-sensitive elements. In some embodiments, a location within the grid of each of the pressure-sensitive elements is specified by a row number and a column number. In some embodiments, the data includes information about a location within the grid of the pressure-sensitive element from which the signal originated.

In any embodiment, each pressure-sensitive element may be substantially circular.

In any embodiment, each pressure-sensitive element may have an average diameter in the range of 0.1 to 5 cm.

In any embodiment, the distance between adjacent pressure sensitive elements may be in the range of 0.5 to 10.0 cm.

In any embodiment, connections between the interconnected pressure-sensitive elements may be substantially straight or undulating.

In any embodiment, the adhesive layer may include soft silicone.

In any embodiment, the multilayered sensing unit may further include a foam layer.

In any embodiment, the multilayered sensing unit may further include a backing layer.

In any embodiment, the multilayered sensing unit may further include a waterproofing layer under the pressure-sensing layer.

In any embodiment, the one or more pressure-sensing devices may include length-wise perforations through one or more layers of the multilayered sensing unit.

In any embodiment, the one or more pressure-sensing devices may include a contoured structure.

In any embodiment, the controller may be configured to transmit the data wirelessly.

In any embodiment, the output unit may include a sound-generating unit configured to generate an alarm sound when a predetermined net number of the one or more threshold criteria are met by the analyzed data.

In any embodiment, the output unit may include a display configured to indicate whether the one or more threshold criteria are met by the analyzed data.

In any embodiment, the computational unit may be at a remote location relative to the location of the one or more pressure-sensing devices and the controller. In some embodiments, the computational unit is a remote server.

Also provided herein is a kit for monitoring a patient, containing: a) one or more pressure-sensing devices, wherein each of the pressure-sensing devices include a pressure-sensitive region configure to: be overlaid on one of one or more pressure ulcer-prone body parts of a body of a patient; and sense force applied to the body part, and wherein each of the pressure-sensing devices is configured to generate data comprising a pressure measurement based on the sensed force; and b) a controller including a communication unit configured to transmit the data generated by the one or more pressure-sensing devices. In some embodiments, each of the pressure-sensing devices includes a multilayered sensing unit containing: a pressure-sensing layer containing an array of interconnected pressure-sensitive elements, wherein each pressure-sensitive element of the array is configured to sense force applied to the body part and generate a signal representative of a magnitude of the force; and an adhesive layer configured to attach the pressure-sensing device to the body part. In some embodiments, the kit further includes a non-transient computer-readable memory containing instructions that, when executed by a processor in a computational unit, cause the computational unit to: i) obtain the data transmitted by the one or more pressure-sensing devices; and ii) analyze the obtained data using one or more threshold criteria, each of the one or more threshold criteria including a threshold value, to determine whether the one or more threshold criteria have been met.

BRIEF DESCRIPTION OF THE FIGURES

The skilled artisan will understand that the drawings, described below, are for illustration purposes only. The drawings are not intended to limit the scope of the present teachings in any way.

FIG. 4 is a schematic drawing of a pressure-sensing layer of a pressure-sensing device, according to embodiments of the present disclosure.

FIG. 11 is a schematic drawing of an array of interconnected pressure-sensitive elements of a pressure-sensing layer of a pressure-sensing device, according to embodiments of the present disclosure.

FIG. 12 is a schematic drawing of an array of interconnected pressure-sensitive elements of a pressure-sensing layer of a pressure-sensing device, according to embodiments of the present disclosure.

DEFINITIONS

Figure 1:
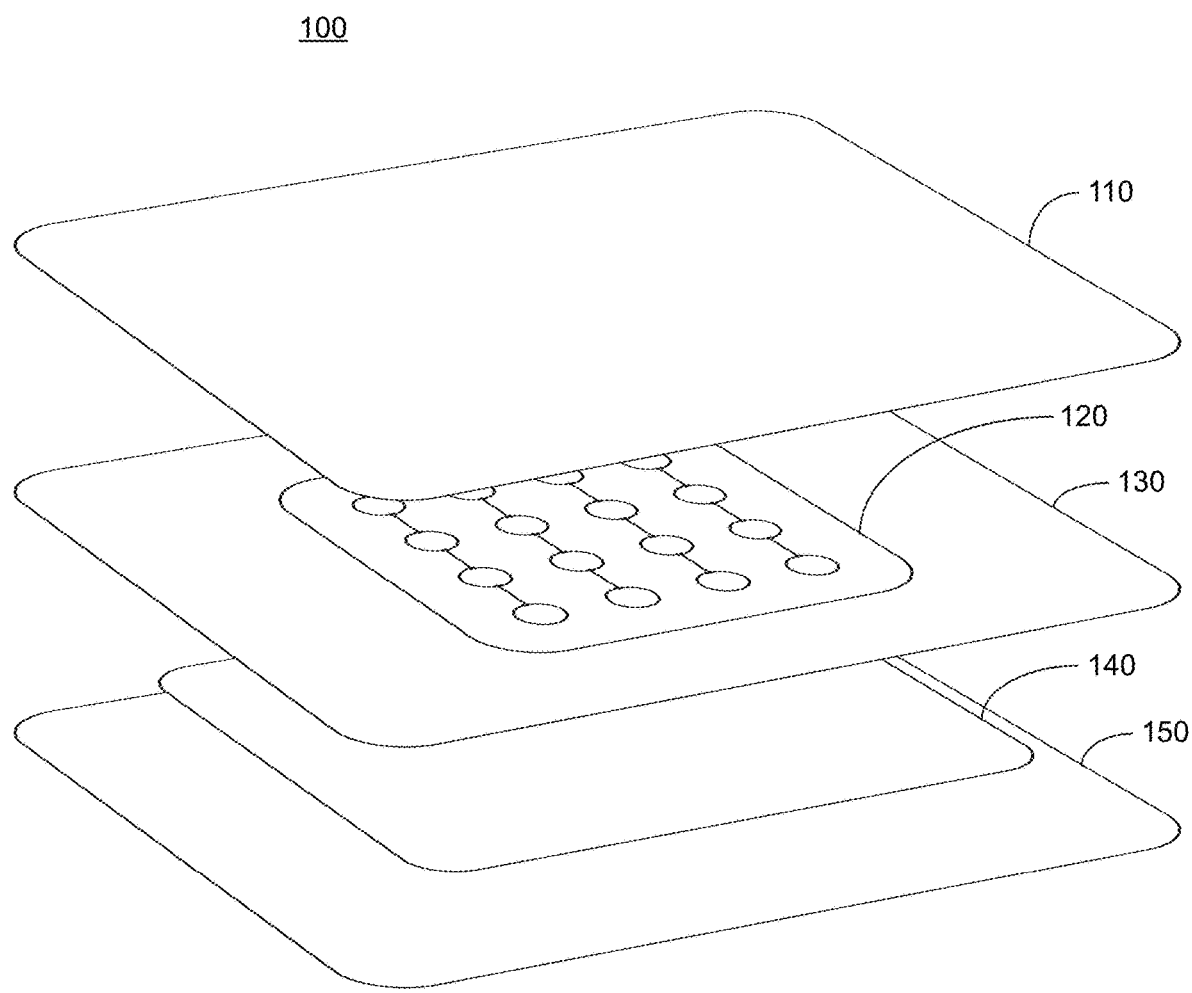
FIG. 1 is a schematic drawing of a pressure-sensitive region and multilayered sensing unit of a pressure-sensing device, according to embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

As used herein "substantially", may be applied to modify any quantitative representation that could permissibly vary without resulting in a change in the basic function to which it is related. For example, two pressure-sensing devices may be located somewhat asymmetrically across a line of symmetry if the recommended intervention provided based on a determination of whether a threshold criteria is met by pressure data from each of the pressure-sensing devices is not materially altered.

"Body part" as used herein, refers to a sub portion of a body of an individual, e.g., a patient. Body part may refer to the external surface of the sub portion of the body.

"Overlie" as used herein, may be applied to describe a spatial relationship between two objects, where a surface of one object is substantially in direct or indirect physical contact along a surface of the other object. The contact between the two objects may be coextensive over a surface of one or the other object, or may be partial, depending on context.

"Selective" as used herein, may be applied to describe the presence of a property in a first subset of a category, which property is less prevalent or absent in a different second subset of the category.

"Transmit" as used herein, refers to an act of transferring information from a sending entity to a receiving entity, where the sending entity and receiving entity are independent information processing entities. The transfer may be through a wireless or wired connection between the entities.

"Array", as used herein, refers to an organization of multiple elements that are in a regular pattern across a surface. "Grid", as used herein, refers to an array where each of the elements is uniquely defined by a row and a column. The row and columns of a grid may be perpendicular to each other in an orthogonal grid.

"Sagittal midline", as used herein, refers to a line bisecting a human body as seen in two dimensions from the front or the back, from the head to the feet.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

DETAILED DESCRIPTION

Provided herein are methods and systems for monitoring, e.g., real-time monitoring, of local pressure applied to different body parts, e.g., pressure ulcer-prone body parts, of a patient. The local pressure applied to the body part may be obtained from a pressure-sensing device that selectively overlies the body part, detects force applied to the body part by a supporting surface, e.g., a bed, and transmits data containing the measured pressure information for analysis. The data may be analyzed, e.g., at a location that is remote from the location of the patient, to determine whether the pressure applied, or pattern of the pressure applied over time, to the body part may increase the risk that the patient will develop a pressure ulcer at the body part being monitored. The analysis may involve comparing the data, or a processed form thereof, to one or more of a series of threshold criteria, and determining the risk of developing a pressure ulcer based on the analysis. Thus, embodiments of the present disclosure provide for continuous and selective monitoring of pressure applied to one or more body parts of a patient, in order to reduce the risk of the patient developing a pressure ulcer.

The patient may be any suitable patient, e.g., an individual who may be at risk of developing a pressure ulcer if left without proper monitoring and intervention. In some cases, the patient is immobile. In some cases the patient is paralyzed, paraplegic, undergoing surgery, systemically or locally anesthetized, elderly, an amputee, comatose, unconscious, brain dead, in a persistent vegetative state, obese, or otherwise immobile due to disease, such as, muscular dystrophy, neurological disease, etc.

The patient may be a patient being monitored by an individual who may be a user of a system as described in the present disclosure and/or by an individual performing a method of the present disclosure. The monitoring individual may be any suitable individual, and may be, without limitation, a healthcare provider, e.g., a physician, nurse practitioner, therapist, chiropractor, physical therapist, occupational therapist, emergency medical technician, social worker; a patient's family member, or any other individual who may be a care taker for the patient.

The pressure ulcer-prone body part may be any body part that is at risk of developing a pressure ulcer in a patient, e.g., an immobile patient. The pressure ulcer-prone body part may be skin that is compressed between a support surface, e.g., a bed, and a bony prominence of the patient when the patient rests on the support surface. Examples of a pressure ulcer-prone body part include, but are not limited to, the occiput, upper back, lower back, elbow, hip, ischium, buttock, knee and the heel.

Further aspects of the present disclosure are now described in detail.

Systems

Figure 17A:
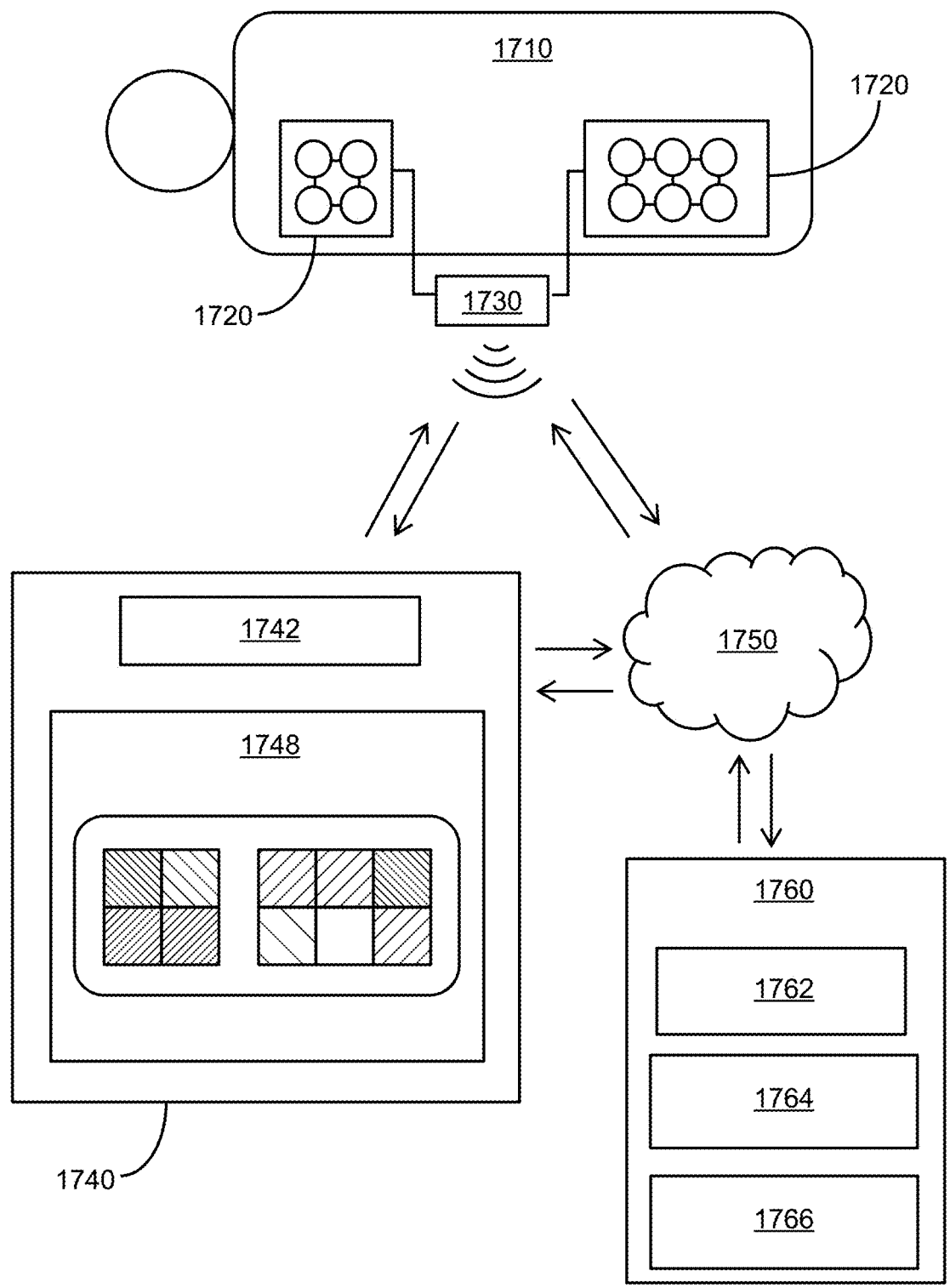
FIGS. 17A and 17B are schematic drawings of a system for monitoring a patient, according to embodiments of the present disclosure.

Aspects of the present system will be described with references to the accompanying figures. With reference to FIG. 17A, the present system may include one or more pressure-sensing devices with a pressure-sensitive region 1720 selectively overlying one or more body parts of a patient 1710. The pressure-sensing device can have a flat profile and be sufficiently flexible so as to conform to the contours of the body part to which it is attached. The pressure-sensing device may include a multilayered sensing unit, which may contain an array of pressure-sensitive regions, as described further herein, and may generate signals, e.g., electrical signals, that are representative of the amount of pressure that is being applied to the body part. Thus, the pressure-sensing device may generate signals representative of the amount of pressure applied to the pressure-sensitive region of the pressure-sensing device when the body part to which the pressure-sensing device is attached is in contact with another surface supporting the patient, e.g., surface of a chair or a bed, or when the body part is not in contact with another surface, e.g. when the patient is standing.

The system may include a controller 1730, e.g., a microcontroller, that is operably connected to the pressure-sensing devices 1720. The controller may be configured to provide the pressure-sensing devices with an electrical signal, e.g., a voltage supply signal, receive from the pressure-sensing device a response signal representative of the pressure applied to the body part, and transmit data that contains the response signal, or a processed form thereof, to a computational unit 1760, e.g., a remote computer, such as a remote server, through a network 1750. In some cases, as shown here, the communication unit includes a wireless communication module to wirelessly transmit the data. The data may be digital and/or analog data. In some cases, the pressure sensing device or the microcontroller may include an analog-to-digital converter, thereby converting an analog electrical signal generated by pressure-sensitive elements of the pressure sensing device, where the analog electrical signal is representative of the pressure applied to the body part of the patient to which the pressure sensing device is attached, into a digital electrical signal representative of the pressure applied to the body part of the patient.

The computational unit 1760 may include a communication module 1762 to receive the data containing information about the amount of pressure that is being applied to the body part sensed by the pressure-sensing device 1720. The computational device may also contain a processor 1764, and a non-transient computer-readable memory 1766 that contains instructions that, when executed by the processor, causes the computational device to obtain the data and analyze them using one or more threshold criteria, to determine whether the one or more threshold criteria have been met, as described herein.

The analyzed data and/or the original pressure data from the pressure-sensing devices may be used to generate an output using a user-interface unit 1740, which may have its own communication unit 1742 to receive and transmit data, analyzed or not. The user-interface unit may include an output unit 1748 configured to present the analyzed or original data to a user, e.g., a medical personnel such as a doctor or a nurse. The output unit may be, e.g., an output display and/or a speaker.

Figure 17B:
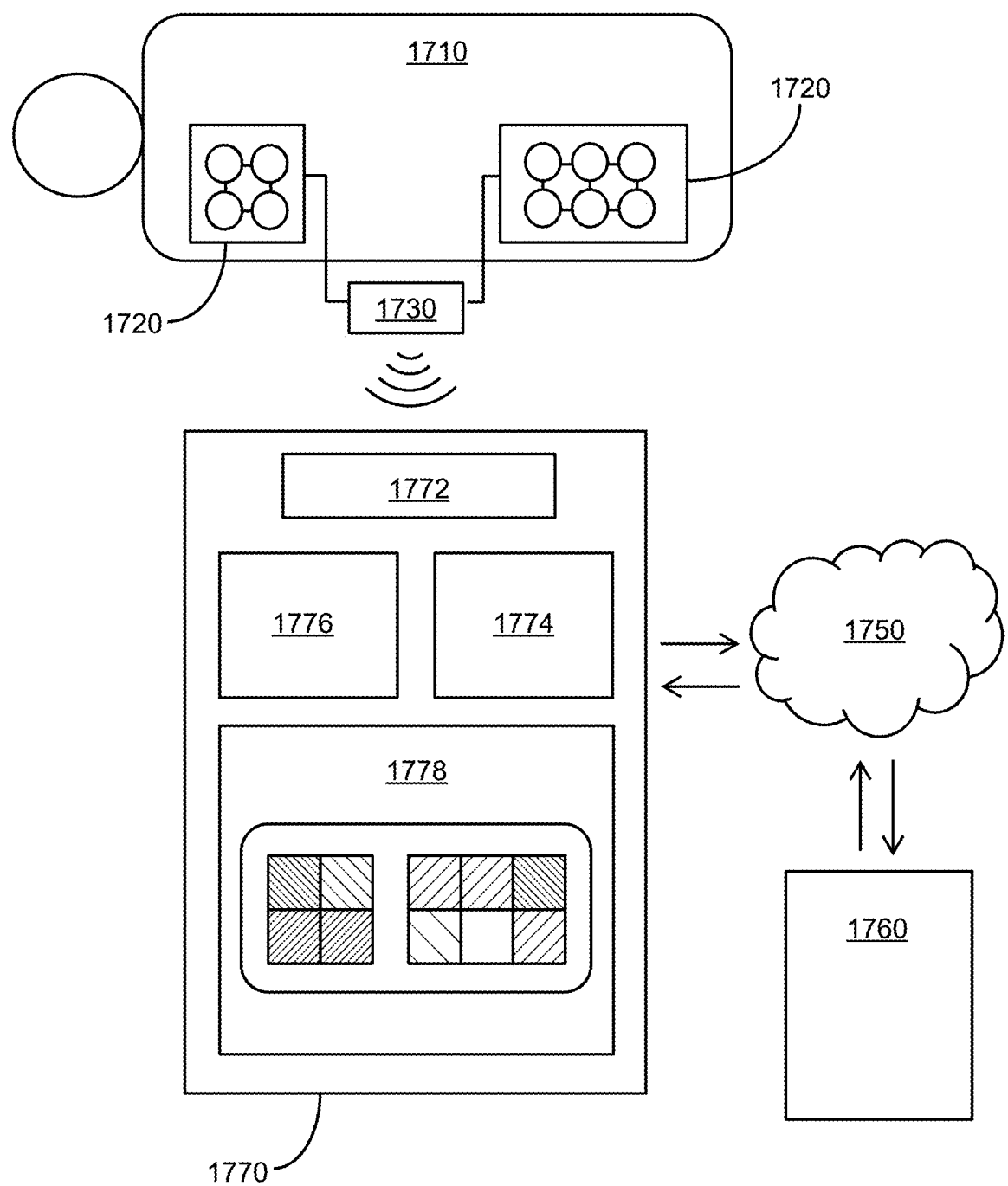

With reference to FIG. 17B, in some cases, the computational unit and the user-interface unit may be an integrated computational/user-interface unit 1770, having a communication unit 1772, processor 1774, a non-transient computer-readable memory 1776 with the instructions, and an output unit 1778. The computational/user-interface unit may be configured to communicate with a remote computer 1760, e.g., a remote database, via a network 1750.

Pressure-Sensing Device

The pressure-sensing device 1720 of the present disclosure may include a pressure-sensitive region and may be configured to sense force applied to the body part and generate data the represents the sensed force. In some embodiments, the pressure-sensing device includes a multilayered pressure-sensing unit, where each of the multiple layers of the pressure-sensing unit can be suitably configured to perform one or more functions suitable for the pressure sensing device. One of the layers may include a pressure-sensing layer that includes an array of interconnected pressure sensors. Another layer may include an adhesive layer that includes an adhesive surface, e.g., a self-adhesive surface, configured to attach at least the pressure-sensitive region, e.g., the area covered by the pressure-sensing unit, of the pressure-sensing device to a body part of the patient.

With reference to FIG. 1, a schematic showing layers of a multi-layered pressure-sensing unit 100 of the pressure sensing device, according to an embodiment of the present disclosure, is shown. The multi-layered pressure-sensing unit may contain a backing layer 110 forming the top layer, i.e., the layer that is furthest away from the surface of the patient's body to which the device is attached. The backing layer may be a breathable backing film, and may be waterproof. The multi-layered pressure-sensing region may contain the pressure-sensing layer 120 under the backing layer, and a waterproof layer 130 under the pressure-sensing layer. The waterproof layer may include, e.g., polyurethane. A foam layer 140 may be disposed under the waterproof layer and may serve to absorb fluid and provide comfort to the patient. The bottom layer may be an adhesive layer 150 configured to attach the multi-layered pressure-sensing unit to the surface of the patient's body part.

The adhesive layer may include any suitable adhesive, e.g., a self-adhesive, to attach at least the pressure-sensitive region of the pressure-sensing device to a body part of the patient. Thus, the adhesive may be suitably disposed on the surface of the adhesive layer that faces the patient's body part. The adhesive may have properties suitable for attaching the pressure-sensing device for an extended period of time, such for 3 days or more, e.g., 5 days or more, including 7 days or more. The adhesive may be biocompatible with the skin of the patient, and non-toxic, non-irritating and non-sensitizing to the skin of the patient. In some cases, the adhesive does not induce significant or any pain, and/or damage to the skin, when the device is removed from the body part of the patient. In some cases, the adhesive is an electrically and/or thermally conductive adhesive. In some embodiments, the adhesive is optically clear, such that the underlying skin may be inspected without removing the pressure-sensing device. In some embodiments, the adhesive layer may include, without limitation, silicone (e.g., soft silicone), acrylic, and non-latex based adhesives. Suitable adhesives are described in, e.g., U.S. Pat. Nos. 5,153,040; 5,540,922; 5,755,681; 8,497,407; and US20040126413, each of which is incorporated herein by reference.

Figure 2A:
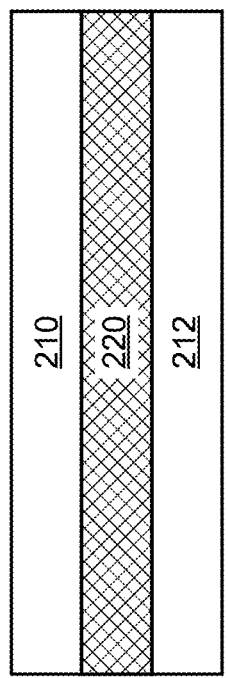
FIGS. 2A and 2B are schematic drawings of a pressure-sensing device, according to embodiments of the present disclosure.

The pressure-sensing layer 120 may be multi-layered. With reference to FIG. 2A, the pressure-sensing layer may include a pressure-sensitive polymer layer 220, e.g., a pressure-sensitive plastic layer, interposed between a first conductive layer 210 and a second conductive layer 212. The pressure-sensitive polymer layer may be a piezoresistive layer, where the electrical resistance of the pressure-sensitive polymer changes based on the pressure applied to the layer. In some cases, the pressure-sensing layer is a capacitive pressure sensor, where an insulating or a dielectric layer is interposed between the first conductive layer and the second conductive layer.

Figure 3A:
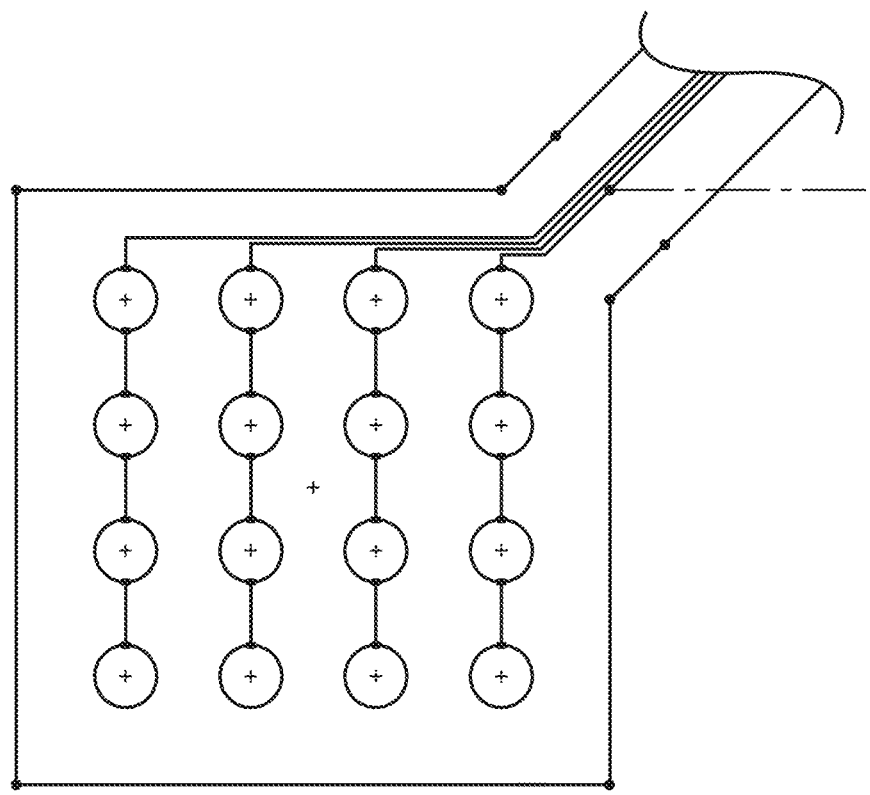
FIGS. 3A-3C are schematic drawings of a pressure-sensitive region of a pressure-sensing device, according to embodiments of the present disclosure.
Figure 3B:
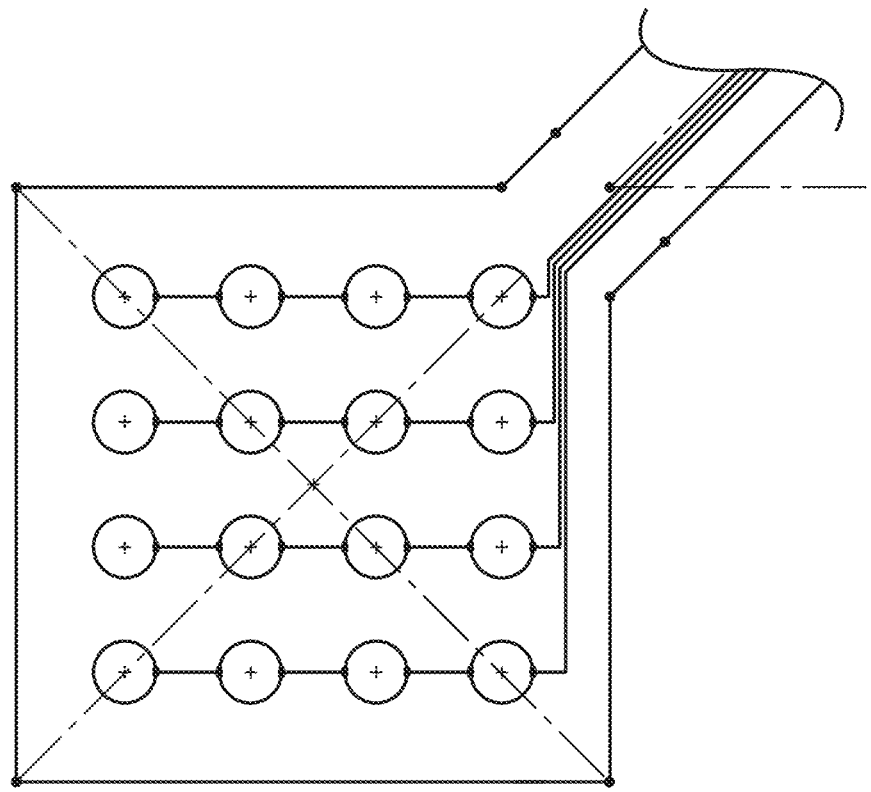
Figure 3C:
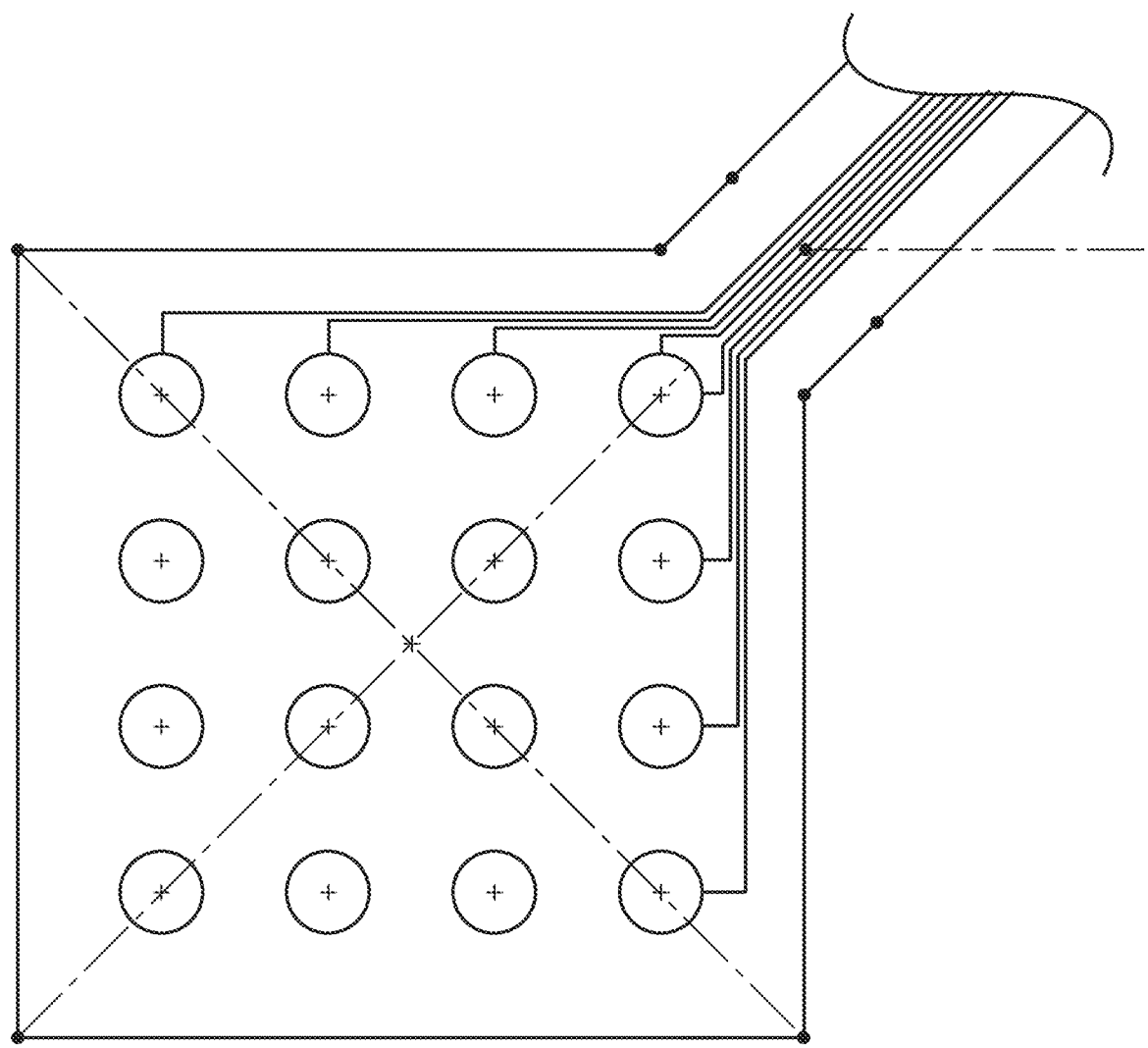
Figure 5:
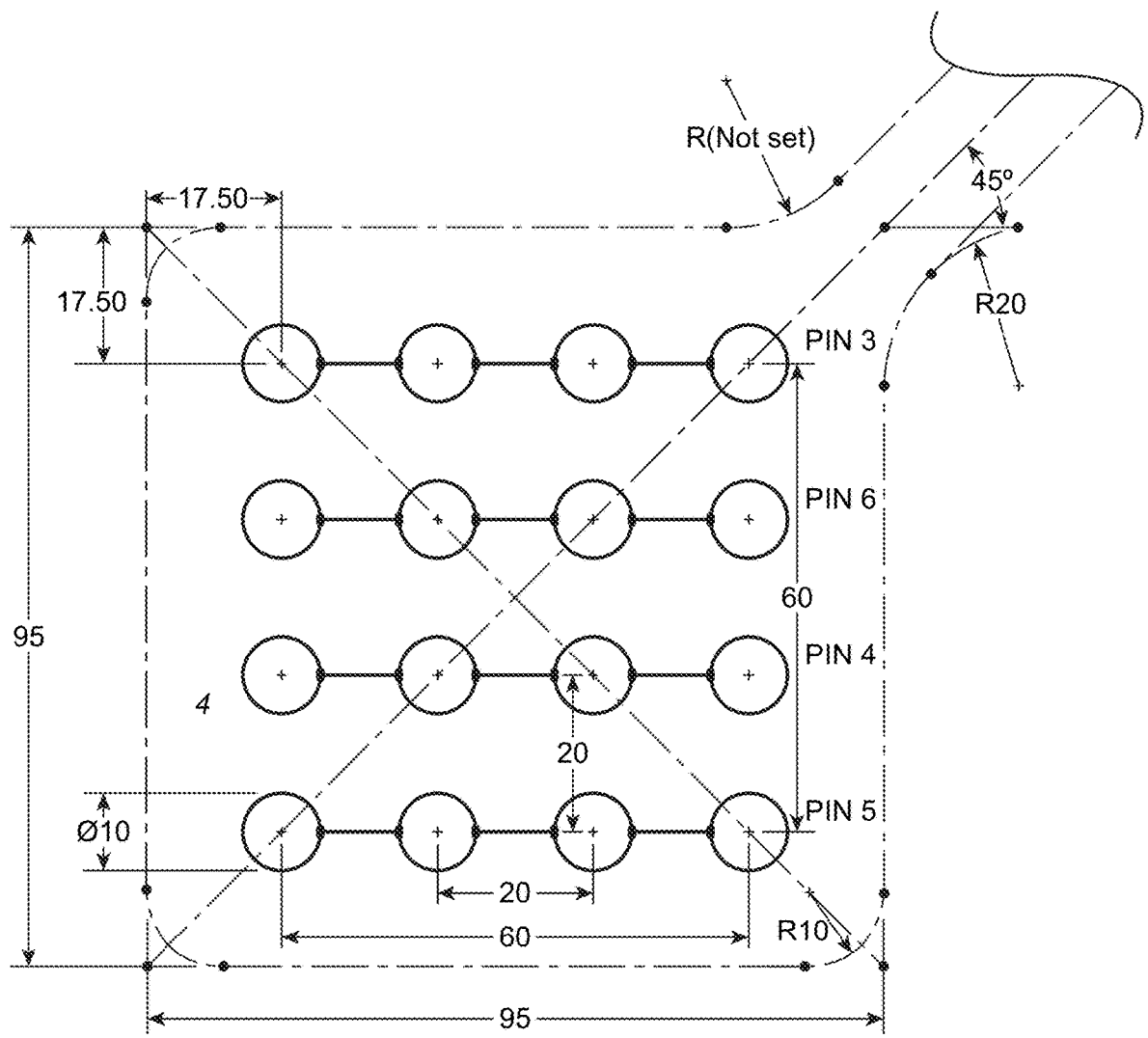
FIG. 5 is a schematic drawing of a pressure-sensitive region of a pressure-sensing device, according to embodiments of the present disclosure.
Figure 6:
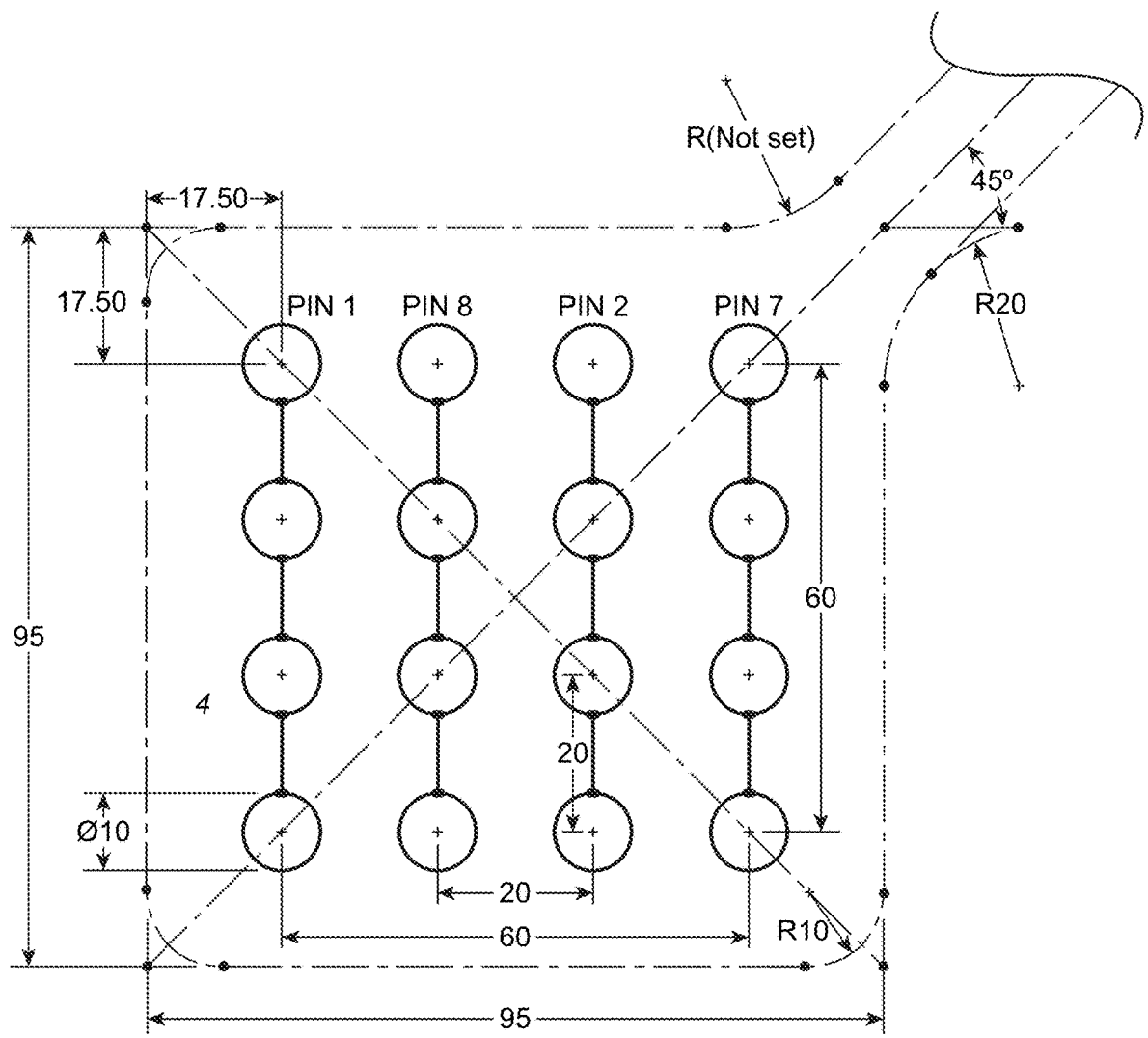
FIG. 6 is a schematic drawing of a pressure-sensitive region of a pressure-sensing device, according to embodiments of the present disclosure.
Figure 7:
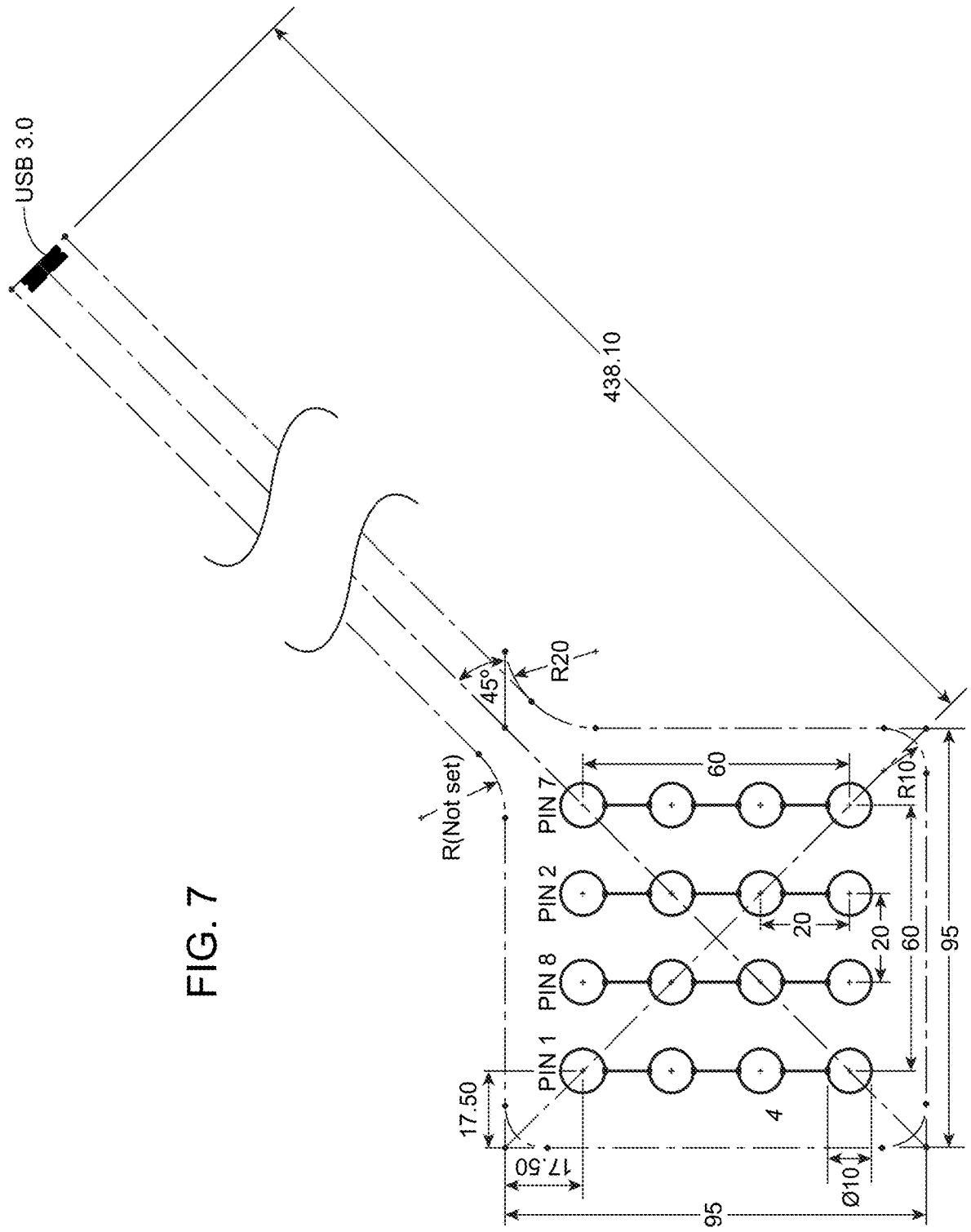
FIG. 7 is a schematic drawing of a pressure-sensitive region and pressure-sensing layer of a pressure-sensing device, according to embodiments of the present disclosure.
Figure 8:
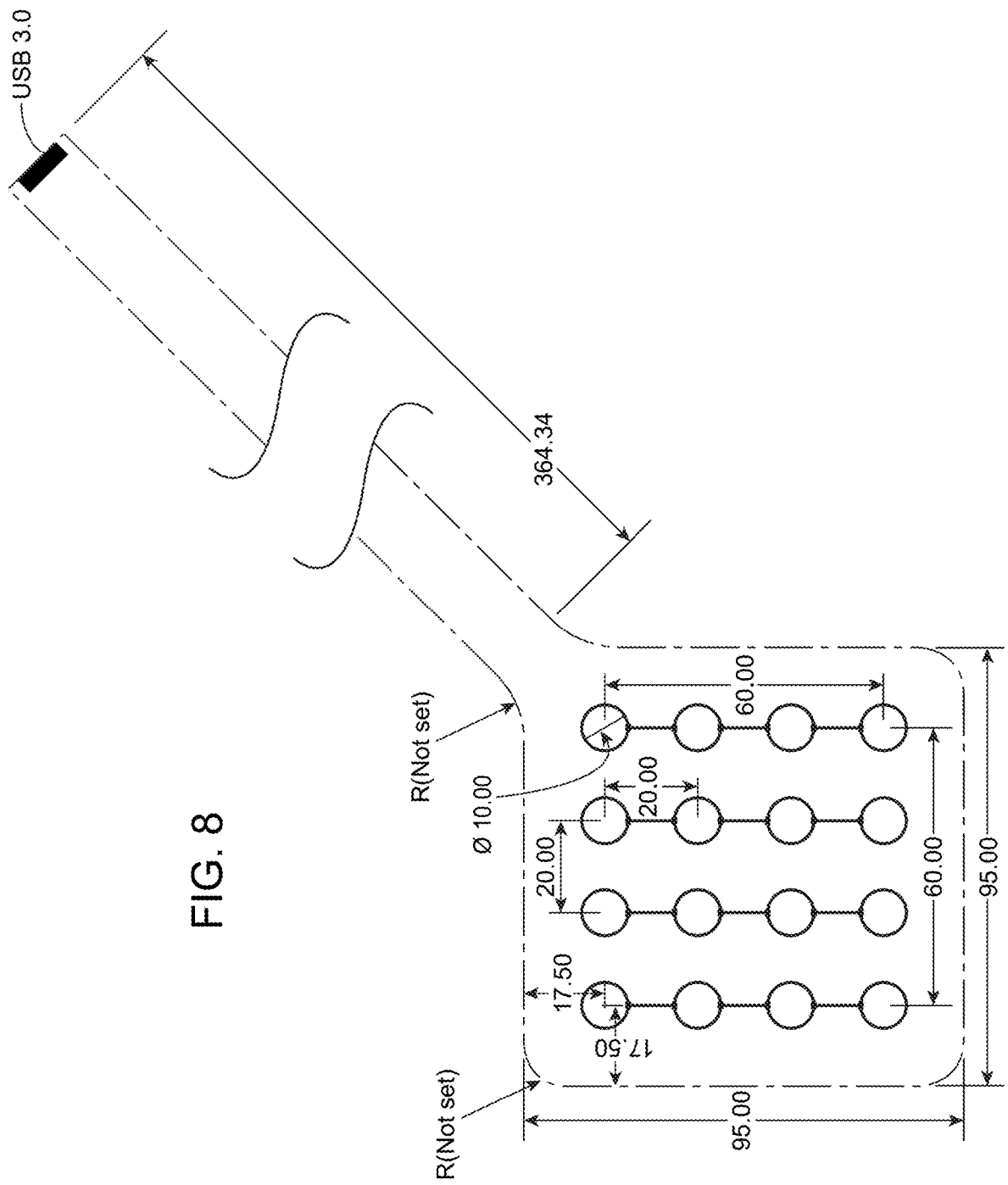
FIG. 8 is a schematic drawing of a pressure-sensitive region and pressure-sensing layer of a pressure-sensing device, according to embodiments of the present disclosure.
Figure 9:
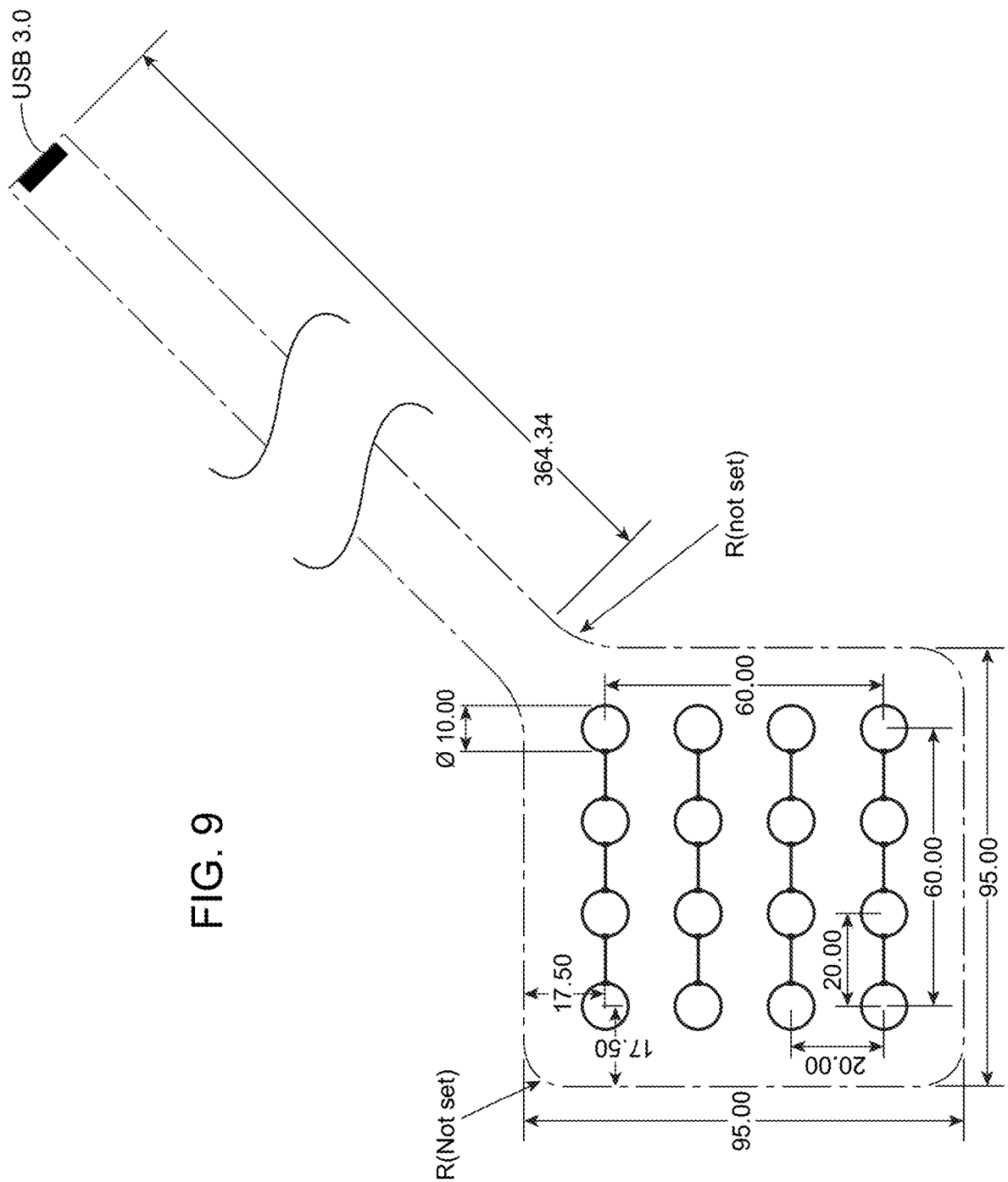
FIG. 9 is a schematic drawing of a pressure-sensitive region and pressure-sensing layer of a pressure-sensing device, according to embodiments of the present disclosure.

FIGS. 3A and 3B (as well as FIGS. 6 and 5) show a schematic view of a surface of the first and second conductive layers, respectively. The conductive layers may include conductive traces patterned as an array of conductive elements, shown here as an array of circular elements, where each of the conductive elements are connected to adjoining conductive element by a connector. The conductive elements on the first and second conductive layers are aligned across the pressure-sensitive polymer layer such that each pair of first and second conductive elements and the intervening pressure-sensitive polymer layer define a pressure-sensitive element. The array of interconnected conductive elements may be arranged as a grid, such that interconnections of the conductive elements of the first conductive layer define one or more columns (FIGS. 3A and 6), interconnections of the conductive elements of the second conductive layer define one or more rows (FIGS. 3B and 5), and such that the location of any given pressure-sensitive element formed by aligning conductive elements of the first and second conductive layers (as shown in FIG. 3C) is defined by the column in which the conductive element of the first conductive layer belongs and the row in which the conductive element of the second conductive layer belongs. Thus, the conductive traces connecting a column of conductive elements in the first conductive layer may be used to provide an electrical input, e.g., an electrical supply voltage, to the entire row, and the conductive traces connecting a row of conductive elements in the second conductive layer may be used to measure the resistance of the circuit of the pressure-sensitive element defined by the column and row.

Figure 2B:
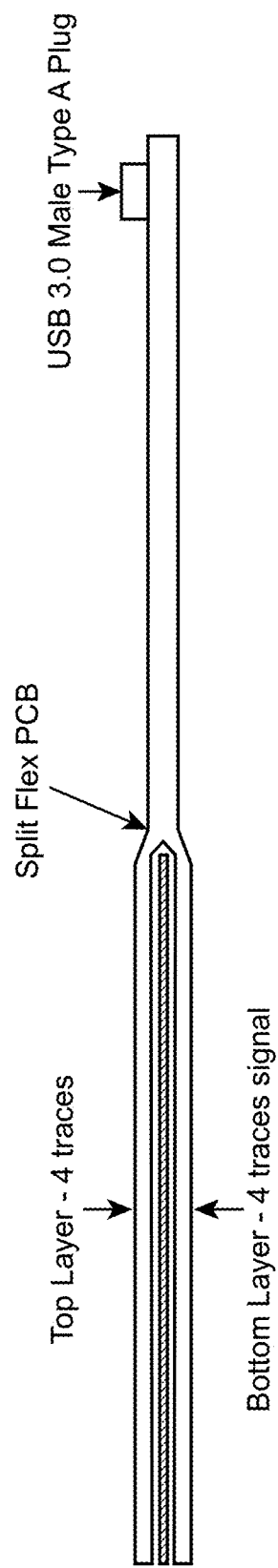

As shown in FIG. 2B, the pressure sensing device having a multilayered pressure-sensing unit may include a substrate that contains the first and second conductive layers at one end that forms a part of the pressure-sensing layer of the multi-layered pressure-sensing unit, and at the other end contains a single-layered portion that merges the first and second conductive layers. The substrate may be, e.g., a flexible printed circuit board (PCB), such as polyimide. An extended view of the surface profile of the substrate containing the first and second conductive layers is shown in FIGS. 4 and 7-9.

Beyond the pressure-sensitive region of the substrate that contains the first and second conductive layers, the conductive traces extend through the single-layered portion, and may terminate at a communication interface, e.g., a universal serial bus (USB) interface (FIGS. 2B and 4).

Figure 10:
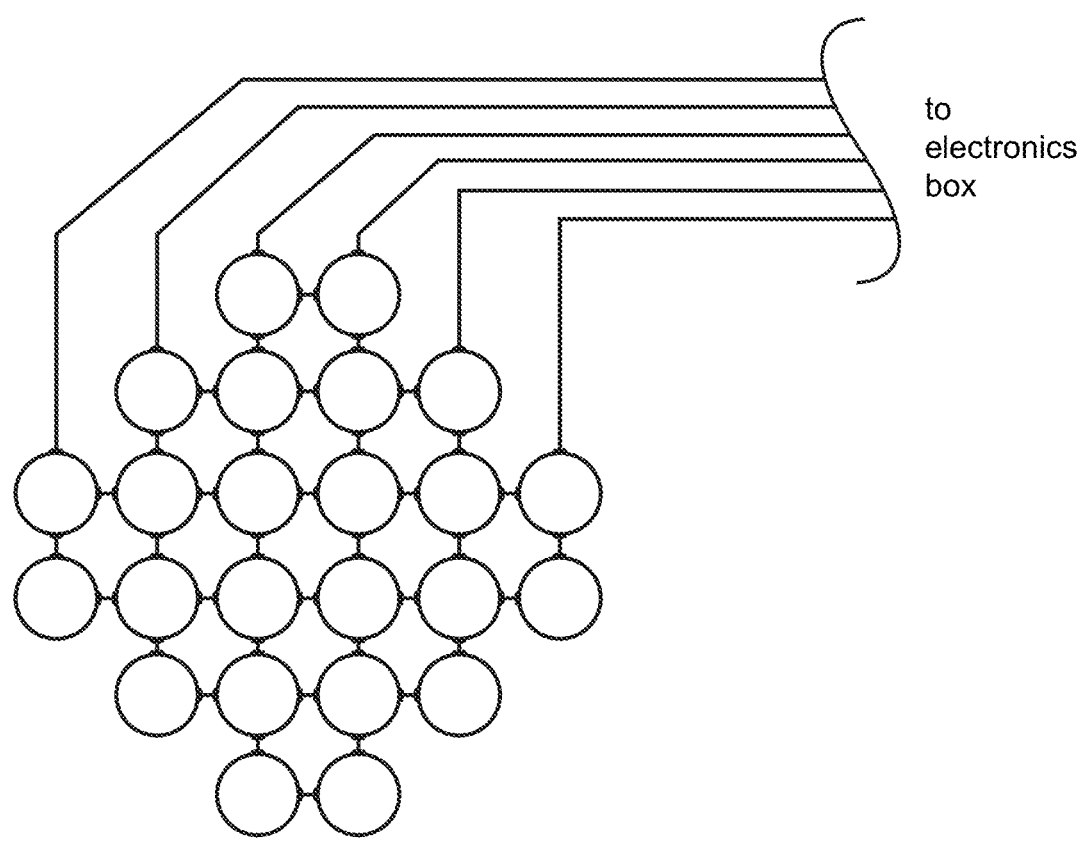
FIG. 10 is a schematic drawing of an array of interconnected pressure-sensitive elements of a pressure-sensing layer of a pressure-sensing device, according to embodiments of the present disclosure.

The pressure-sensitive elements in the array of the pressure-sensing device of the present disclosure may be arranged in any suitable fashion. The pressure-sensitive elements may be organized as a circular array, square array, rectangular array, diamond array, triangular array, hexagonal array, octagonal array, etc., or an irregular-shaped array (FIGS. 10-12, 14-16A-B). In some embodiments, the pressure-sensitive elements are arranged to match the shape of the surface of the body part that comes into contact with a support surface (FIGS. 14, 15 and 16A-B). In some cases, the pressure-sensitive elements are arranged to overlie the surface of the left or right shoulder blades that contacts a support surface (FIG. 14), to overlie the surface of the buttock and/or hip area that contacts a support surface (FIG. 15), or to overlie the surface of the elbow, knee, ischium or heel that contacts a support surface (FIG. 10). Any convenient shape may be generated using a suitably large array of pressure-sensitive elements, and removing excess conductive elements from the first and/or second conductive surfaces (FIGS. 11 and 12).

Figure 13:
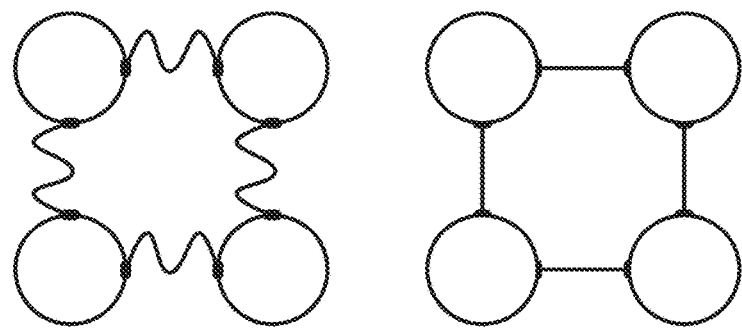
FIG. 13 is a schematic drawing of an array of interconnected pressure-sensitive elements of a pressure-sensing layer of a pressure-sensing device, according to embodiments of the present disclosure.
Figure 14:
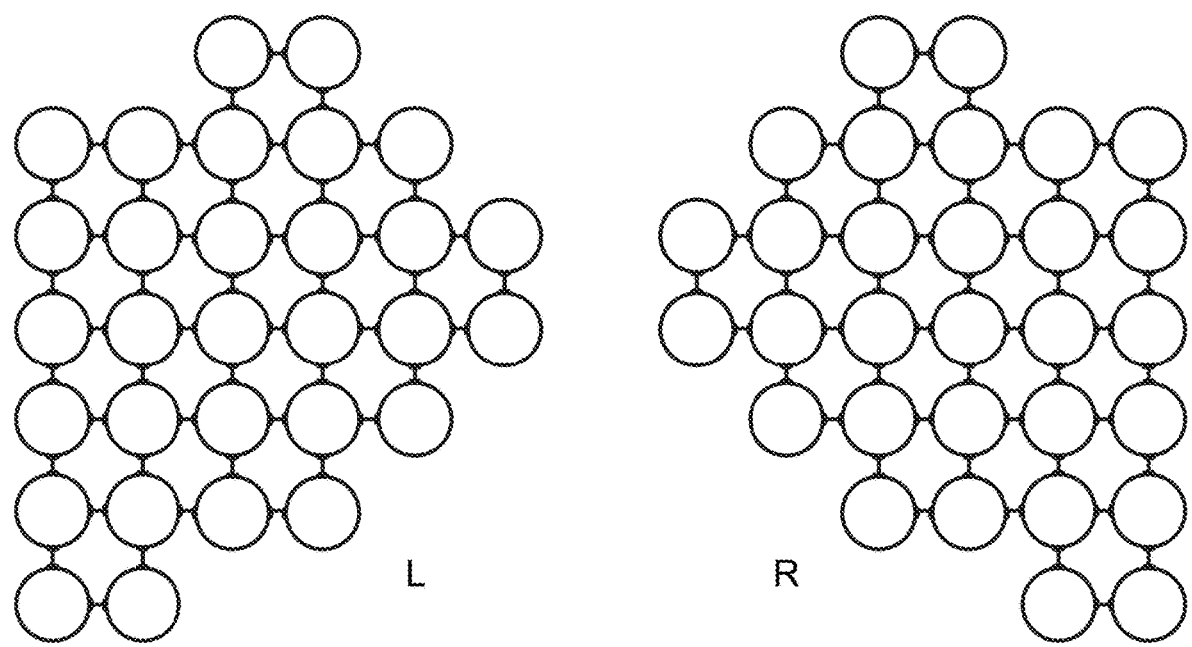
FIG. 14 is a schematic drawing of an array of interconnected pressure-sensitive elements of a pressure-sensing layer of a pressure-sensing device, according to embodiments of the present disclosure.
Figure 15:
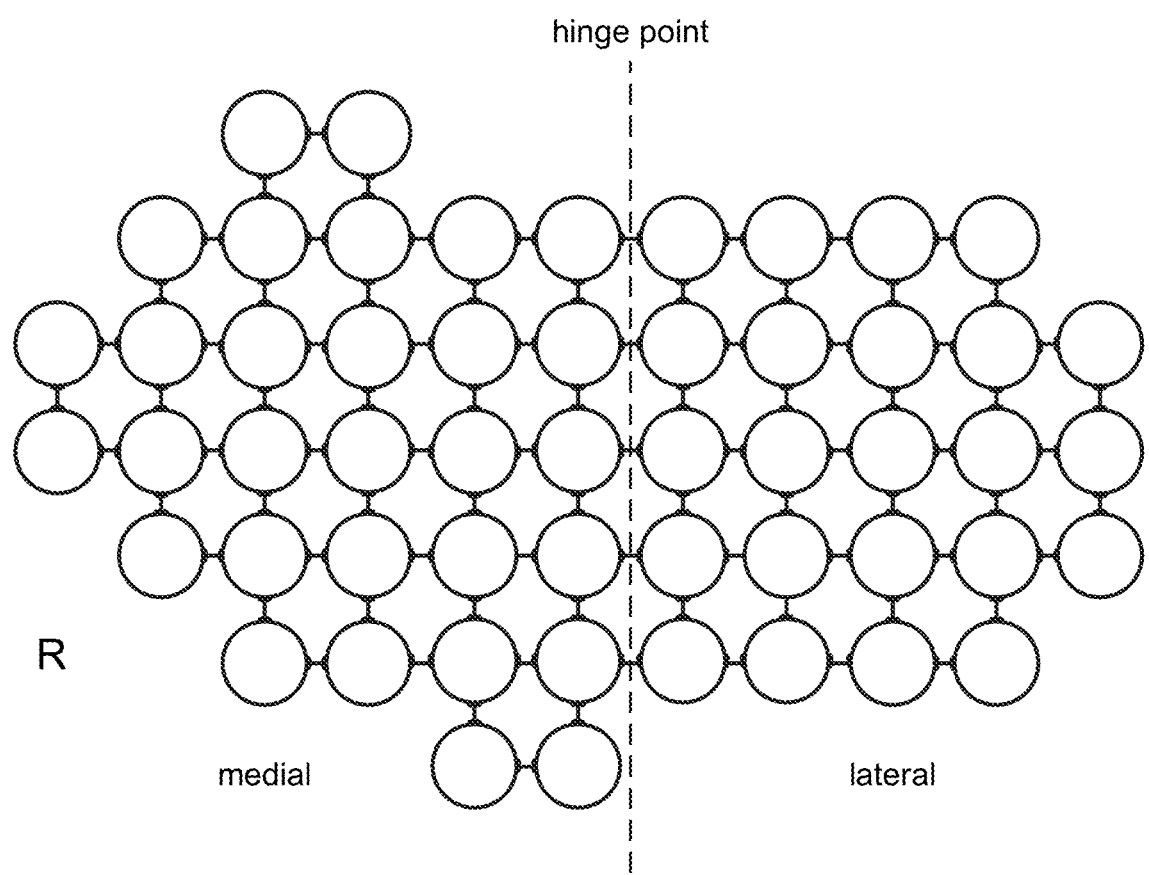
FIG. 15 is a schematic drawing of an array of interconnected pressure-sensitive elements of a pressure-sensing layer of a pressure-sensing device, according to embodiments of the present disclosure.

The connectors connecting adjoining conductive elements may have any suitable shape (FIG. 13). The connectors may be defined as the sections of the conductive trace in between the conductive elements that have a narrower width than the average diameter or width of the conductive elements. The width of the connector, as defined to as a cross-section of the connector along a line perpendicular to the direction of current flow through connector, may be 0.5 fold or less, e.g., 0.4 fold or less, 0.3 fold or less, 0.2 fold or less, 0.1 fold or less, 0.05 fold or less, 0.01 fold or less, including 0.001 fold or less than the average diameter or width of the conductive element. In some cases, the connectors are straight. In some cases, the connectors are not straight, and may be sinusoidal or may be undulating, which may provide more flexibility for the pressure-sensing device compared to the straight connectors.

Figure 16A:
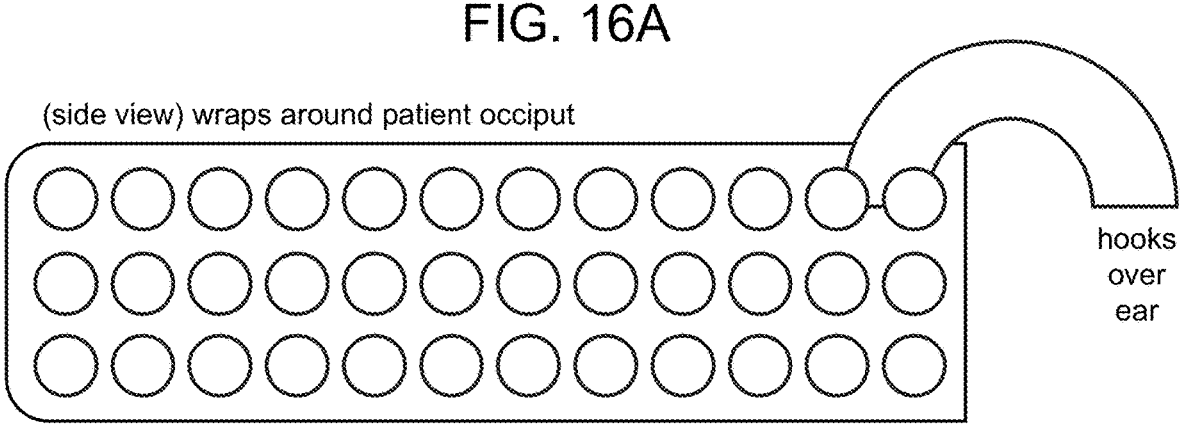
FIGS. 16A and 16B are schematic drawings of a pressure-sensing device, according to embodiments of the present disclosure.

In some cases, the pressure-sensing device includes shaped or contoured structures that facilitate attaching, registering and/or aligning the device to the body part. In some embodiments, the contoured structure is a curved structure located at an end of a pressure-sensing device designed to monitor pressure applied to the patient's occiput, where the curved structure may hook onto the patient's ear to facilitate alignment of the pressure-sensitive region of the pressure-sensing device with the occiput (FIG. 16A).

Figure 16B:
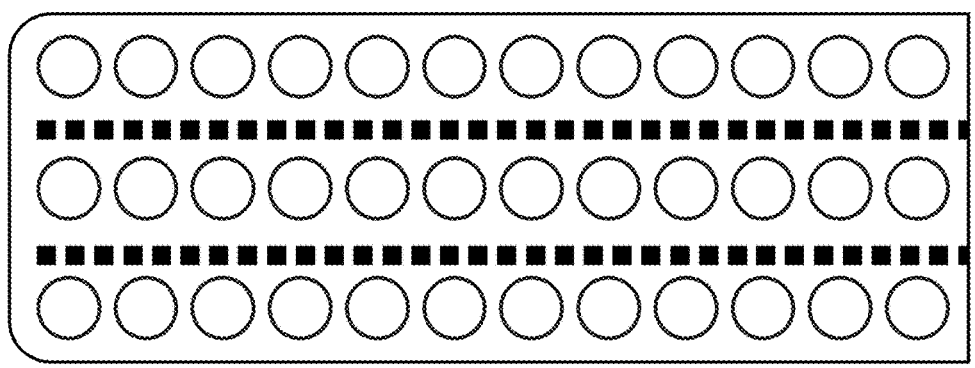

The pressure-sensing device may include any other suitable modification to facilitate attaching, registering and/or aligning the device to the body part. In some embodiments, the pressure-sensing device may include perforations in one or more layers contained therein to increase the flexibility of the device and/or match the contours of the body part (FIG. 16B).

The pressure-sensing device may be a substantially flat structure so that the device can be overlaid along a patient's body part that contacts and is supported by a supporting surface, such as a surface of a bed. The average thickness of the multi-layered sensing unit may be any suitable thickness. In some cases, the average thickness of the multi-layered sensing unit is 0.5 mm or more, e.g., 1.0 mm or more, 1.5 mm or more, 2.0 mm or more, including 2.5 mm or more, and is 3.0 mm or less, e.g., 2.5 mm or less, 2.0 mm or less, 1.5 mm or less, 1.0 mm or less, including 0.5 mm or less. In some cases, the average thickness of the multi-layered sensing unit is in the range of 0.5 to 3.0 mm, e.g., 0.5 to 2.5 mm, including 0.5 to 2.0 mm.

The pressure-sensitive polymer may have any convenient thickness. In some cases, the average thickness of the pressure-sensitive polymer is 20 µm or more, e.g., 30 µm or more, 40 µm or more, 50 µm or more, 60 µm or more, including 70 µm or more, and is 200 µm or less, e.g., 150 µm or less, 100 µm or less, 90 µm or less, including 80 µm or less. In some cases, the average thickness of the pressure-sensitive polymer is in the range of 20 to 200 µm, e.g., 20 to 150 µm, 30 to 100 µm, 40 to 90 µm, including 50 to 90 µm.

The average thickness of the foam layer may be any suitable thickness. In some cases, the average thickness of the foam layer is 0.1 mm or more, e.g., 0.3 mm or more, 0.5 mm or more, 0.8 mm or more, including 1 mm or more, and is 2.5 mm or less, e.g., 2.0 mm or less, 1.5 mm or less, including 1.0 mm or less. In some cases, the average thickness of the foam layer is in the range of 0.1 to 2.5 mm, e.g., 0.5 to 2.0 mm, including 0.5 to 1.5 mm.

The lateral dimensions of the present pressure-sensing device may have any suitable lengths. The average diameter of the pressure-sensing device (e.g., the diameter of a circle that circumscribes the shape of the pressure-sensing device) may be 1 cm or more, e.g., 3 cm or more, 6 cm or more, 10 cm or more, 15 cm or more, including 20 cm or more, and may be 50 cm or less, e.g., 40 cm or less, 30 cm or less, 20 cm or less, including 10 cm or less. In some cases, the average diameter of the pressure-sensing device is in the range of 1 to 50 cm, e.g., 3 to 40 cm, 6 to 30 cm, including 6 to 20 cm. Where the pressure-sensing device has a substantially rectangular shape for the multi-layered sensing unit, the width and/or length of the multi-layered sensing unit may be 1 cm or more, e.g., 3 cm or more, 6 cm or more, 10 cm or more, 15 cm or more, including 20 cm or more, and may be 50 cm or less, e.g., 40 cm or less, 30 cm or less, 20 cm or less, including 10 cm or less. In some embodiments, the width and/or length of the multi-layered sensing unit is in the range of 1 to 50 cm, e.g., 3 to 40 cm, 6 to 30 cm, including 6 to 20 cm.

Where the pressure-sensing device has a substantially rectangular shape for the pressure-sensitive layer, the width and/or length of the pressure-sensitive layer may be 1 cm or more, e.g., 3 cm or more, 6 cm or more, 10 cm or more, 12 cm or more, including 15 cm or more, and may be 45 cm or less, e.g., 35 cm or less, 25 cm or less, 15 cm or less, including 5 cm or less. In some embodiments, the width and/or length of the pressure-sensitive layer is in the range of 1 to 45 cm, e.g., 3 to 35 cm, 6 to 25 cm, including 6 to 15 cm.

The pressure-sensitive region, e.g., the area covered by the pressure-sensing unit of the pressure-sensing device, may overlie any suitable size area of the patient's body part. In some cases, the pressure-sensitive region overlies an area of 1.0 cm$^2$ or more, e.g., 2.0 cm$^2$ or more, 5.0 cm$^2$ or more, 10 cm$^2$ or more, 50 cm$^2$ or more, 100 cm$^2$ or more, including 1,000 cm$^2$ or more, and overlies an area of 10,000 cm$^2$ or less, e.g., 3,000 cm$^2$ or less, 1,000 cm$^2$ or less, 500 cm$^2$ or less, 200 cm$^2$ or less, 100 cm$^2$ or less, including 50 cm$^2$ or less. In certain embodiments, the pressure-sensitive region overlies an area in the range of 1.0 to 10,000 cm$^2$, e.g., 2.0 to 3,000 cm$^2$, 5.0 to 1,000 cm$^2$, 5.0 to 500 cm$^2$, including 10 to 200 cm$^2$.

The pressure-sensitive region, e.g., the area covered by the pressure-sensing unit of the pressure-sensing device, may selectively overlie any suitable proportion of a pressure ulcer-prone body part of a patient. In some embodiments, the pressure-sensitive region overlies at least 50%, e.g., at least 60%, at least 70%, at least 80%, at least 90%, at least 95%, and up to 100% of a pressure ulcer-prone body part.

The pressure-sensitive layer interposed between the first and second conductive layers may have any convenient form. In some cases, the pressure-sensitive layer is in the form of a film, a sheet, or a mesh. In some cases, the pressure-sensitive layer is monolithic (i.e., contains no gaps or large holes in the structure), and is substantially contiguous over the area covered by the array of pressure-sensitive elements.

The pressure-sensitive layer may include any suitable number of pressure-sensitive elements. In some cases, the pressure-sensitive layer includes 1 or more, e.g., 2 or more, 3 or more, 5 or more, 10 or more, 15 or more, 20 or more, 30 or more, including 50 or more pressure-sensitive elements, and includes 10,000 or fewer, e.g., 1,000 or fewer, 500 or fewer, 100 or fewer, including 50 or fewer pressure-sensitive elements. In some embodiments, the pressure-sensitive layer includes 1 to 10,000, e.g., 2 to 1,000, 3 to 500, 5 to 100, including 10 to 100 pressure-sensitive elements.

The average thickness of the pressure-sensitive element may be any suitable thickness. In some cases, the average thickness of the pressure-sensitive element is 0.10 mm or more, e.g., 0.20 mm or more, 0.30 mm or more, 0.35 mm or more, including 0.40 mm or more, and is 2.0 mm or less, e.g., 1.0 mm or less, 0.80 mm or less, 0.70 mm or less, including 0.60 mm or less. In some cases, the average thickness of the pressure-sensitive element is in the range of 0.10 to 2.0 mm, e.g., 0.20 to 1.0 mm, including 0.30 to 0.80 mm.

The pressure-sensitive elements may have any suitable surface shape and lateral dimensions. The shape of the pressure sensitive element may be circular, oval, square, rectangular, triangular, diamond, hexagonal, octagonal, etc., or may be an irregular shape. The average diameter of the pressure sensitive element (e.g., the diameter of a circle that circumscribes the shape of the pressure sensitive element) may be 0.1 cm or more, e.g., 0.3 cm or more, 0.5 cm or more, 0.75 cm or more, including 1 cm or more, and may be 5.0 cm or less, e.g., 4.0 cm or less, 3.0 cm or less, 2.0 cm or less, including 1 cm or less. In some cases, the average diameter of the pressure sensitive element is in the range of 0.1 to 5.0 cm, e.g., 0.3 to 4.0 cm, 0.5 to 3.0 cm, including 0.5 to 2.0 cm.

The distance between adjacent pressure sensitive elements (i.e., distance from the center of one pressure sensitive element to the center of another pressure sensitive element in a row or column immediately adjacent to the first pressure sensitive element) may be any suitable length. In some cases, the distance between adjacent pressure sensitive elements is 0.5 cm or more, e.g., 0.75 cm or more, 1.0 cm or more, 1.5 cm or more, including 2.0 cm or more, and is 10.0 cm or less, 7.5 cm or less, 5.0 cm or less, 4.0 cm or less, 3.0 cm or less, 2.5 cm or less, including 2.0 cm or less. In some embodiments, the spacing between adjacent pressure sensitive elements is in the range of 0.5 to 10.0 cm, e.g., 0.75 to 7.5 cm, 1.0 to 5.0 cm, 1.0 to 3.0 cm, including 1.5 to 2.5 cm.

The pressure-sensing device may include any suitable material that allows for the device to function as a pressure-sensing device and that allows for the device to be a compliant structure that sufficiently conforms to the contours of the patient's body part. The substrate for forming the conductive layers may include any suitable flexible substrate. In some cases, the substrate is a flexible PCB that includes, but not limited to, polyimide, polyether ether ketone (PEEK), or conductive polyesters, such as polyethylene terephthalate (PET).

The pressure-sensitive polymer may include any suitable piezoresistive polymer. The pressure-sensitive polymer may be a composite polymer, i.e., a polymer that includes a conductive filler that alters the resistivity of the polymer in a pressure and/or strain-dependent manner. The polymer may be a synthetic or a natural polymer. Any suitable synthetic polymer may be used, such as, but not limited to, polyester, polybutadiene, polyisoprene, polyurethane, nylon, polyethylene, and silicone. Any suitable natural polymer may be used, such as, but not limited to, cellulose, starch, rubber, chitin, etc. The conductive filler may be any suitable conductive filler, such as, but not limited to, silver particles, gold particles, carbon nano-tubes, carbon black, etc. In some cases, the pressure-sensitive polymer includes a carbon-base thermoforming plastic.

The pressure-sensing element may have any suitable dynamic range. In some cases, the pressure-sensing device has a dynamic range of 100 lb./in$^2$ or less, e.g., 50 lb./in$^2$ or less, 20 lb./in$^2$ or less, 10 lb./in$^2$ or less, 5.0 lb./in$^2$ or less, 3.0 lb./in$^2$ or less, including 1.0 lb./in$^2$ or less. In certain embodiments, the pressure-sensing device has a dynamic range of 0 to 1.0 lb./in$^2$, e.g., 0 to 5.0 lb./in$^2$, including 0 to 10 lb./in$^2$.

The pressure-sensing device may be configured to have a suitable dynamic range for sensing pressure applied to the pressure-sensing device by a body part of a patient. In some embodiments, the pressure-sensing device is configured to detect a weight of 200 lb. or less, e.g., 175 lb. or less, 150 lb. or less, 125 lb. or less, including 100 lb. or less. In some embodiments, the pressure-sensing device is configured to detect a weight in the range of 0 to 200 lb., e.g., 0 to 150 lb., including 0 to 125 lb.

The present disclosure also contemplates any other suitable pressure-sensing devices for use in the present method, systems and kits, as described further herein. In some cases, the pressure-sensing device is a capacitive, electromagnetic, or a piezoelectric pressure sensor. In one illustrative, non-limiting embodiment, a thin-film resistive force sensor may be used, e.g., a FlexiForce® load sensor, which is available from Tekscan, Inc. of Boston, Mass.

The present system may include any number of pressure-sensing devices, which may be in communication with a single or multiple controllers, as necessary. In some cases, the system includes one or more, e.g., 2 or more, 3 or more, 4 or more, 5 or more, 8 or more, 12 or more, including 15 or more, and includes 50 or fewer, e.g., 40 or fewer, 30 or fewer, 20 or fewer, 10 or fewer, including 6 or fewer pressure-sensing devices. In some embodiments, the system includes 1 to 50, e.g., 1 to 30, 1 to 10, including 2 to 6 pressure-sensing devices.

The present pressure-sensing device may also include additional data processing, communication unit, and/or memory units, any or any combination of which may be used to process the signal from the pressure-sensing device before the data containing a processed signal is transmitted.

Controller

The controller may be any suitable device that can operably connect to a pressure-sensing device and transmit data from the pressure-sensing device to a computational unit. The controller may include an appropriate mating interface (e.g., an appropriate USB interface) for connecting with the communication interface of the pressure-sensing device. In some cases, the controller may be configured such that an appropriate voltage signal is provided to the communication interface channels (e.g., USB pins) corresponding to the columns/rows of the array of pressure-sensitive elements in the pressure-sensing layer, and such that the response signal is read from the communication interface channels (e.g., USB pins) corresponding to the rows/columns of the array. In some cases, the controller is a microcontroller.

The controller may be configured to be positioned at a site that is remote from where the pressure applied to the patient's body part is being sensed, i.e., at a site that is remote from the pressure-sensitive region of the pressure-sensing device. The controller may in some cases be attached to the patient, at a site that is remote from the pressure-sensitive region. In some embodiments, a controller may be configured to communicate with multiple pressure-sensing devices, each located at different body parts, e.g., pressure ulcer-prone body parts, of the patient. In some cases, the controller is in communication with one or more, e.g., 2 or more, 3 or more, 4 or more, 6 or more, 8 or more, 12 or more, including 15 or more, and is in communication with 50 or fewer, e.g., 40 or fewer, 30 or fewer, 20 or fewer, 10 or fewer, including 6 or fewer pressure-sensing devices.

In some embodiments, the controller is in communication with 1 to 50, e.g., 1 to 30, 1 to 10, including 2 to 6 pressure-sensing devices.

The controller may include a communication unit configured to transmit the data obtained from the pressure-sensing device to a computational unit. The communication unit may be any suitable communication unit, and may employ any suitable method of communicating with a computational unit, such as, but not limited to, Bluetooth®, Wi-Fi, Ethernet, USB, IEEE 1394, etc.

The controller may include a power source, e.g., a battery, a power adaptor, or any other suitable power source, to provide the electrical signal that powers the pressure-sensing device. In some cases, controller includes a processor, a memory, etc.

The transmission of the data may be achieved by any convenient method. In some cases, the communication unit includes a wireless communication module to wirelessly transmit the data. In some cases, the communication unit has a wired connection to the computational device.

Computational Unit

A generalized example of a computational unit of a system of the present disclosure, and in which the methods of the present disclosure can be implemented, is depicted in FIGS. 17A and 17B. A computational unit 1760/1770 of the present system may be any suitable computational unit configured to receive data generated by the pressure-sensing devices 1720 and transmitted by the controller 1730. The computational unit may include a user-interface 1740/1770 that contains an output unit 1748/1778 that is configured to display results of the analysis of the patient's pressure data. Thus, in certain embodiments, the computation unit and the user-interface may be separate units, or contained in the same unit.

The memory 1766/1776 can be any form of memory device, for example, volatile or non-volatile memory, solid state storage devices, magnetic devices, etc. In certain aspects, the memory includes a non-transitory storage medium (e.g., a storage medium that is not a transitory wave or signal). The processor 1764/1774 can contain more than one distinct processing device, for example to handle different functions within the computational unit 1760/1770. The computation unit and/or user-interface unit may include any suitable input devices to receive input data, and can include, for example, a keyboard, a pointer device such as a pen-like device or a mouse, audio receiving device for voice controlled activation such as a microphone, data receiver or antenna such as a modem or wireless data adaptor, data acquisition card, etc. Input data can come from different sources, for example keyboard instructions in conjunction with data received via a network.

Output unit 1748/1778 produces/generates/displays output data and can include, for example, a display device or monitor in which case output data is visual, a printer in which case output data is printed, a port for example a USB port, a peripheral component adaptor, a data transmitter or antenna such as a modem or wireless network adaptor, etc. Output data can be distinct and derived from different output devices, for example a visual display on a monitor in conjunction with data transmitted to a network. A user can view data output, or an interpretation of the data output, on, for example, a monitor or using a printer.

In use, a user-interface unit 1740 or a computational unit 1770 may be adapted to allow data or information to be stored in and/or retrieved from, via wired or wireless communication means, at least remote computer 1760.

The user-interface unit 1740, the remote computer 1760, and the computational unit 1770 may be a part of a networked communications system. User-interface unit 1740, and computational unit 1770 can connect to a network, for example the Internet or a wide area network (WAN). Input data and output data can be communicated to other devices via the network. The transfer of information and/or data over the network can be achieved using wired communications means or wireless communications means. A server can facilitate the transfer of data between the network and one or more databases. A server and one or more databases provide an example of an information source.

Thus, the computing system environment illustrated in FIGS. 17A and 17B may operate in a networked environment using logical connections to one or more remote computers. The remote computer may be a personal computer (PC), a server, a router, a network PC, a peer device, or other common network node, and typically includes many or all of the elements described above.

FIGS. 17A and 17B are intended to provide a brief, general description of an illustrative and/or suitable example of a computing environment in which embodiments of the methods disclosed herein may be implemented. FIGS. 17A and 17B are examples of a suitable environment and are not intended to suggest any limitation as to the structure, scope of use, or functionality of an embodiment of the present disclosure.

Certain embodiments may be described with reference to acts and symbolic representations of operations (e.g., such as the flow diagrams shown in FIGS. 18-25) that are performed by one or more computing devices, such as the computing system environment of FIGS. 17A and 17B. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of well-known computing systems, environments, and configurations that may be suitable for use with an embodiment include, but are not limited to, personal computers, handheld or laptop devices, tablets, cell phones, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as program modules, being executed by a computer. Generally, program modules include routines, programs, objects, components, data structures, etc., that perform particular tasks or implement particular abstract data types.

Computer Program Products

The present disclosure provides computer program products that, when executed on a programmable computer such as that described above with reference to FIGS. 17A and 17B, can carry out the methods of the present disclosure. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" (e.g., "computer-readable medium") refers to any computer program product, apparatus and/or device (e.g., magnetic discs, optical disks, memory, etc.) used to provide machine instructions and/or data to a programmable processor, including a machine-readable medium that receives machine instructions as a machine-readable signal. According to certain embodiments, the machine-readable medium is non-transitory (e.g., a machine readable medium that is not a transitory wave or signal).

It will be apparent from this description that aspects of the present disclosure may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium (e.g., a non-transitory computer-readable medium) including any type of ROM, RAM, cache memory, network memory, floppy disks, hard drive disk (HDD), solid-state devices (SSD), optical disk, CD-ROM, Blue-ray Disc™ and magnetic-optical disk, EPROMs, EEPROMs, flash memory, or any other type of media suitable for storing instructions in electronic format.

Methods

Also provided herein is a method of monitoring a patient, e.g., using a system for monitoring a patient as described above. In general terms, the present method includes obtaining pressure data from one or more pressure-sensing devices attached to the body of a patient in need of monitoring, e.g., a patient at risk of developing a pressure ulcer; analyzing the data using one or more threshold criteria; and generating an output that indicates whether the one or more threshold criteria are met based on the analysis of the pressure data. The pressure data may be analog and/or digital data.

The pressure sensing device may be any suitable device for sensing pressure. In some cases, the pressure sensing device includes a multilayered sensing unit, as described above, which can be attached and laid flat against a body part, e.g., a pressure ulcer-prone body part, of a patient. The pressure sensing device may include an array of interconnected pressure-sensitive elements. In some cases, the pressure-sensitive elements are arranged in a grid, as shown, e.g., in FIG. 3C, and FIGS. 10-11, such that the force applied to the body part at the position corresponding to a pressure-sensitive element can be determined by applying a current to the column (or row) of the pressure-sensitive element and measuring the signal at the row (or column) of the pressure-sensitive element. The signal measured at the pressure-sensitive element, defined by the coordinates of the row and column, may be converted to a force based on a predetermined conversion factor, where the conversion factor may be obtained by a suitable calibration process using force of known magnitude applied to the pressure-sensitive element.

Figure 18:
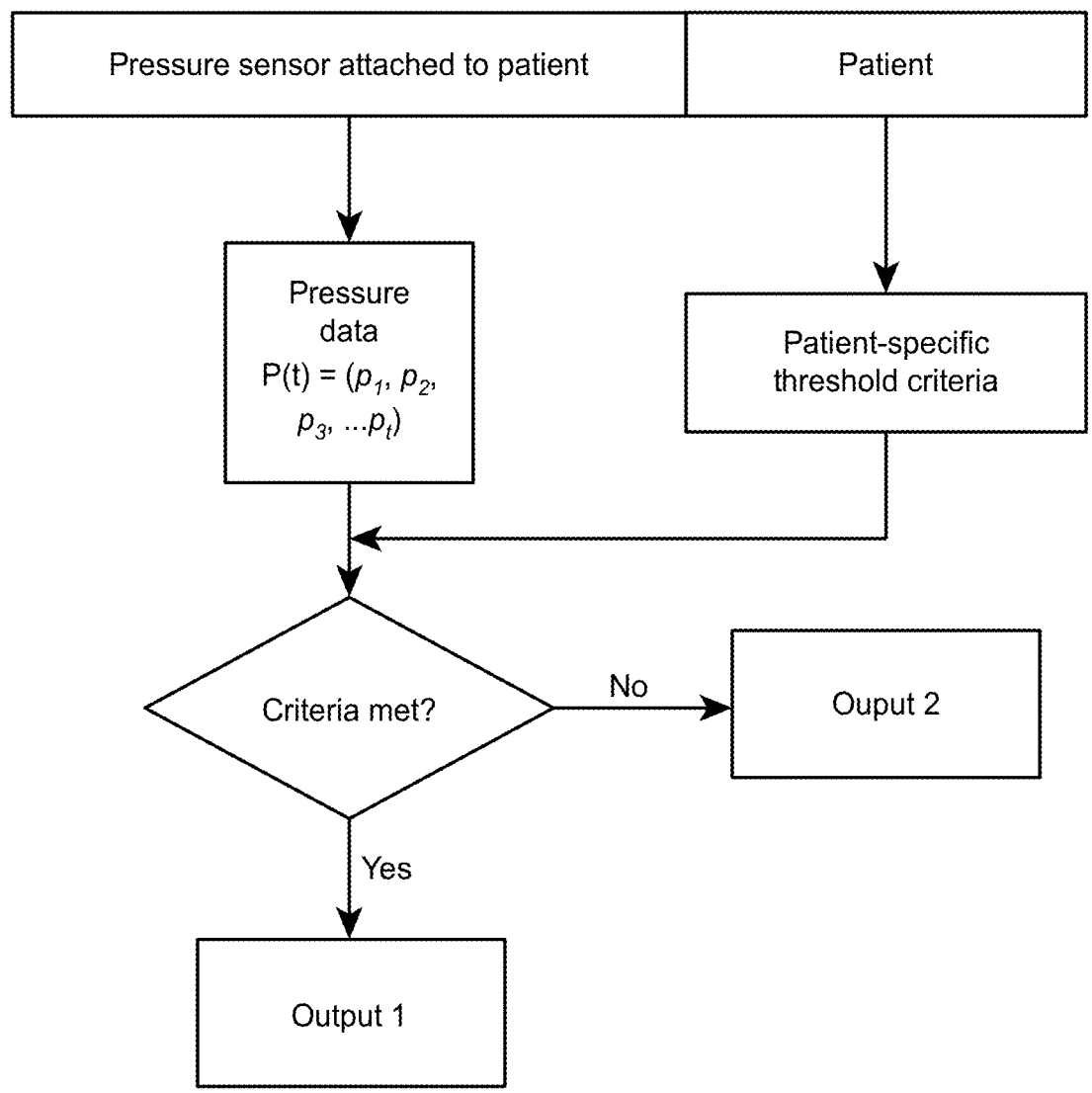
FIG. 18 is a flow chart depicting an algorithm for monitoring a patient, according to embodiments of the present disclosure.

Embodiments of the present method may be further described with reference to FIGS. 18-25. With reference to FIG. 18, a patient may have one or more pressure-sensing devices attached to an appropriate location on the patient's body, e.g., a body part that is prone to develop a pressure ulcer because of exposure of the body part to continuous and prolonged periods of applied pressure. The threshold criteria may be defined by threshold values, and a given criteria may be met when the pressure data, or processed forms thereof, give measured values that are above or below the threshold values, depending on the threshold criterion. If a threshold criterion is met by the pressure data obtained from the patient, a first output may be generated, and if the threshold criterion is not met, a second output may be generated.

The analysis may involve analyzing an instantaneous pressure reading obtained at a single time point from the pressure sensing device. In addition, the pressure data may be obtained continuously from the patient to generate a series of pressure readings from the pressure-sensing device, and the analysis may involve analyzing pressure data from one or more time points in the series. In some cases, the data obtained from the pressure-sensing device contains a voltage output, and the voltage output may be converted to a pressure value (i.e., force per unit area value) using a suitable calibration standard. The calibration standard may be a predetermined calibration standard for the pressure-sensing device.

The threshold criteria can be patient-specific threshold criteria, and may include patient-specific threshold values. The patient-specific threshold criteria may be pre-determined based on risk-factors for pressure ulcer development that are present or absent in the patient. The patient-specific risk factors may include, but are not limited to, age, immobility, diabetes, peripheral vascular disease (PVD), cardiac failure, kidney failure, neurological disorder, malnutrition, sepsis, incontinence, spinal cord injury, anemia, skin condition, prolonged surgery, weight loss, obesity and combinations thereof. In some cases, the patient-specific risk factors may include age, diabetes, PVD, kidney failure, sepsis, incontinence, spinal cord injury, anemia, skin condition, weight loss, obesity, time since admission, type of admission, albumin, prealbumin, CRP, creatinine, glucose, sodium, potassium, bicarbonate, blood urea nitrogen, white blood cell count, hematocrit, platelet count, total bilirubin, pH, pCO2, pO2, FiO2, hemoglobin A1c, urine output, history of acute renal failure, history of paralytic drug use, days of paralytic drug use, history of vasoactive drug use, days of vasoactive drug use, heart rate, mean arterial pressure, systolic blood pressure, diastolic blood pressure, respiration rate, oxygenation, temperature (max/min), Glasgow Coma Score, history of mechanical ventilation or other positive pressure ventilation, days of ventilator use, history of incontinence, days of incontinence, history of metastatic cancer, history of hematologic malignancy, history of AIDS, history of severe organ system insufficiency or immunocompromised status, and history of spinal cord injury leading to paresis or paralysis, and combinations thereof.

Figure 19:
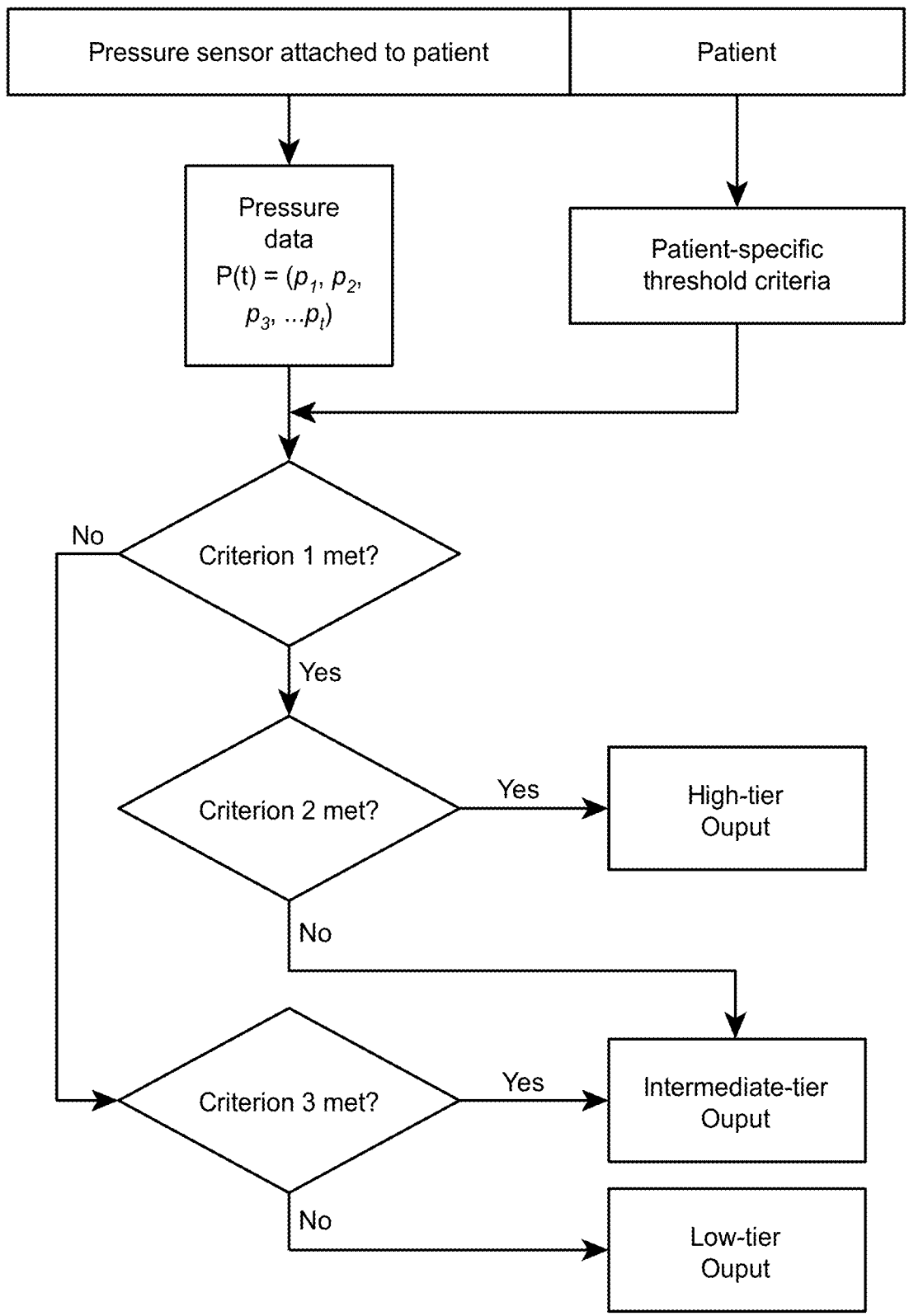
FIG. 19 is a flow chart depicting an algorithm for monitoring a patient, according to embodiments of the present disclosure.

With reference to FIG. 19, an embodiment of the present method is described. In some cases, multiple threshold criteria (e.g., criteria 1-3) may be used to analyze the pressure data obtained from a patient. The data may be analyzed against two or more of the threshold criteria in a sequence. The output from the analysis may include a tiered output such that the output provides an indication of how many threshold criteria have been met by the pressure data. In some cases, the tiered output provides an indication of the net number of threshold criteria that have been met—i.e., ([the total number of threshold criteria that have been met]−[the total number of threshold criteria that have not been met])—by the pressure data. For example, if the net number of threshold criteria that have been met is 2 (e.g., criteria 1 and 2 are met), a high-tier output may be generated; if the net number of threshold criteria that have been met is 0 (e.g., criterion 1 is met, and criterion 2 is not met; or criterion 1 is not met and criterion 3 is met), an intermediate-tier output may be generated; and if the net number of threshold criteria that have been met is −2 (e.g., criteria 1 and 3 are not met), a low-tier output may be generated.

Figure 20:
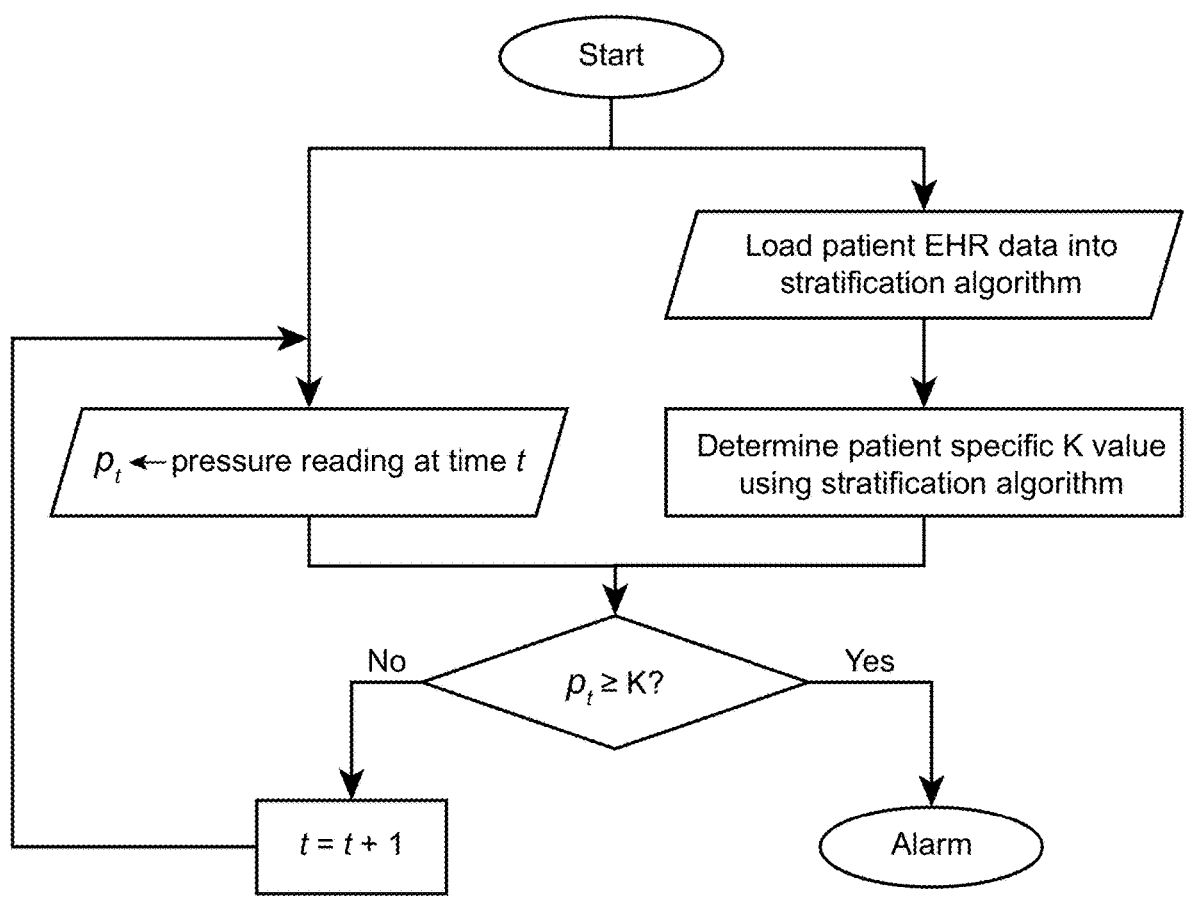
FIG. 20 is a flow chart depicting an algorithm for monitoring a patient, according to embodiments of the present disclosure.

In some cases, determining whether a threshold criterion has been met by pressure data obtained from a patient, where the analysis of the pressure data is performed on a pressure reading from a single time point, i.e., an instantaneous pressure reading. With reference to FIG. 20, there is shown a flow chart for determining whether a threshold criterion has been met by analyzing an instantaneous pressure reading, according to embodiments of the present disclosure. Risk variables, e.g., risk factors for developing pressure ulcers, for the patient may be determined from the patient's medical records, e.g., the patient's electronic health record (EHR). Based on the patient's medical records, a patient-specific threshold value, κ, for pressure may be derived using a stratification algorithm that takes the patient's medical records as input. At time t, a pressure reading ($p_t$) may be obtained. The threshold criterion may be met if $p_t$ is equal to or greater than κ, or the threshold criterion may not be met if $p_t$ is less than κ. If the threshold criterion is met, an output, e.g., a visual or an auditory alarm signal, may be generated, the output indicating that the threshold criterion has been met. If the threshold criterion is not met, the analysis may proceed for the next pressure reading.

Figure 21:
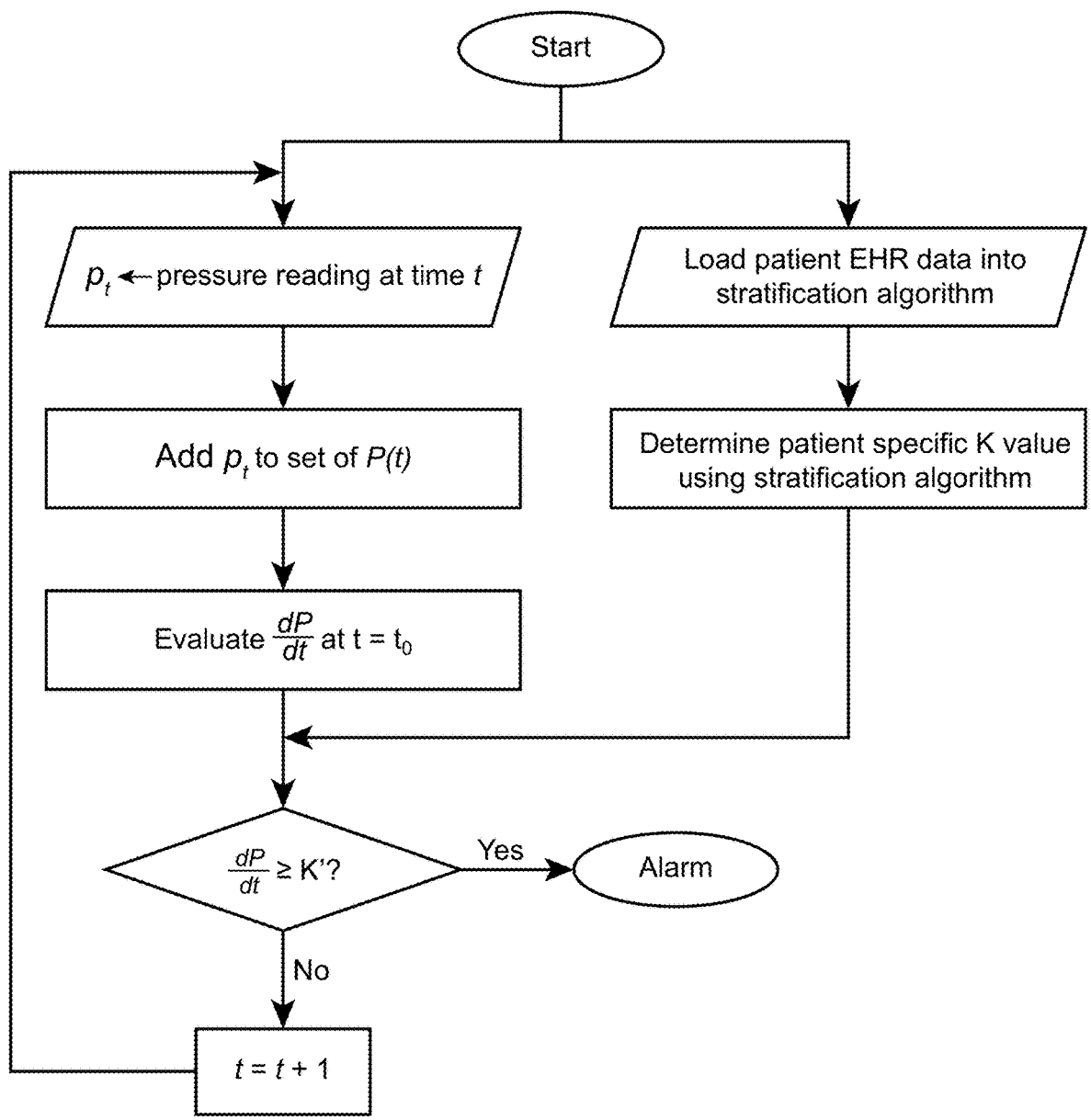
FIG. 21 is a flow chart depicting an algorithm for monitoring a patient, according to embodiments of the present disclosure.

The analysis may in some cases include analyzing pressure readings from multiple time points, e.g., analysis of a time series of pressure readings. FIG. 21 shows a flow chart for determining whether a threshold criterion has been met by pressure data obtained from a patient, according to embodiments of the present disclosure, where the analysis involves calculating the rate of change in the pressure measurements. Risk variables may be obtained from the patient's medical records, as described above, and the patient-specific risk variables may be passed through a stratification algorithm to derive a patient-specific threshold value, κ', for the first derivative of pressure (as a function of time), i.e., the pressure change over time, using the patient's medical records as input to the stratification algorithm. A pressure reading may be obtained at a number of time points $t_1, t_2, \ldots t_n$, where n is an integer greater than 1, to generate a time series of pressure measurements $P(t)=(p_{t_1}, p_{t_2}, \ldots, p_{t_n})$. The threshold criterion may be met if the first derivative of P(t):

$$\frac{dP(t)}{dt}$$

evaluated at $t=t_0$, where $t_0$ may be the time of a contemporaneous pressure reading, e.g., the most recent pressure reading, is equal to or greater than κ', or the threshold criterion may not be met if $$\frac{dP(t)}{dt}$$

evaluated at $t=t_0$, is less than κ'. If the threshold criterion is met, an output may be generated, as described above, intended to indicate to an individual, e.g., an individual monitoring the patient that the threshold criterion has been met. If the threshold criterion is not met, the analysis may proceed for the next pressure reading.

Figure 22:
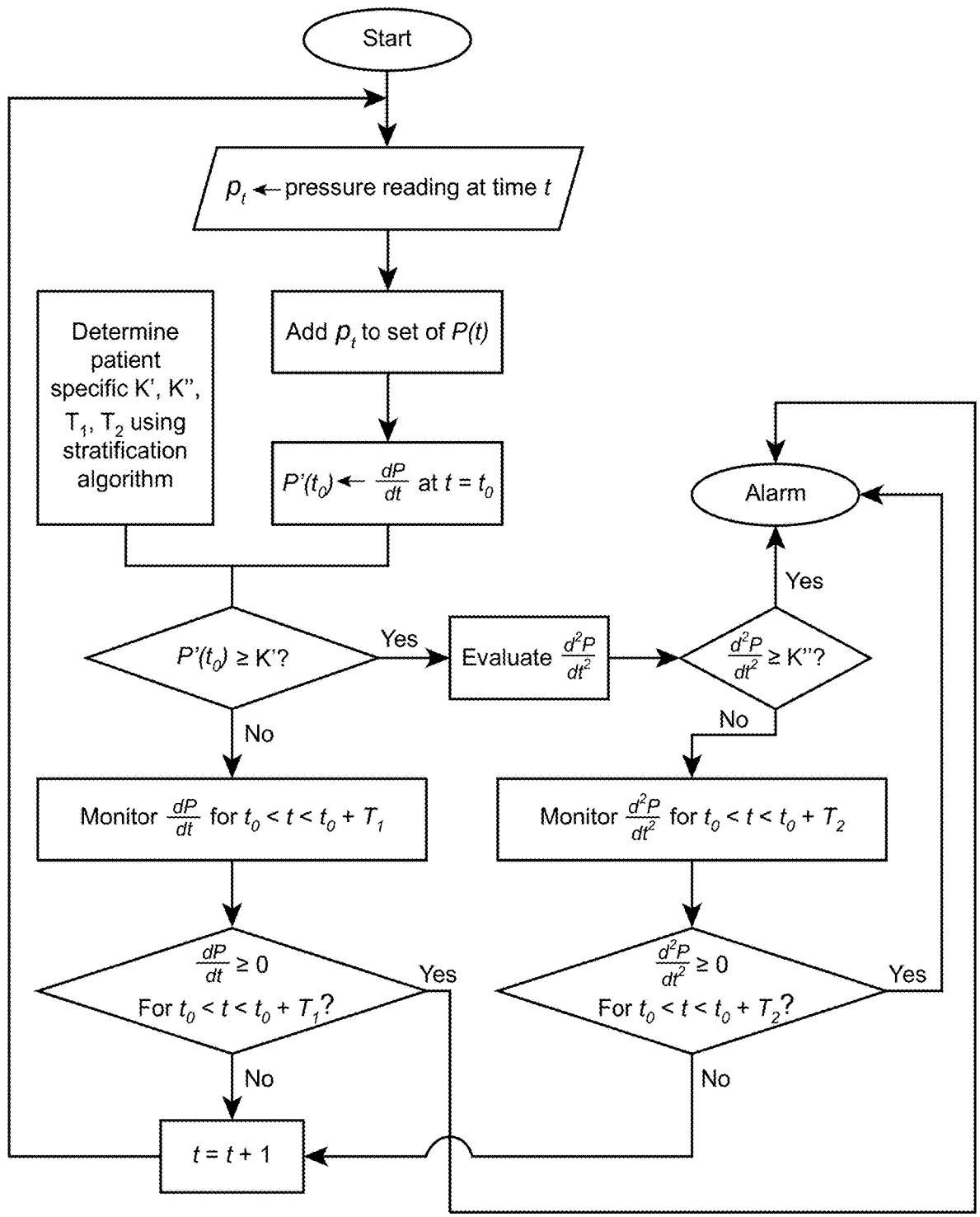
FIG. 22 is a flow chart depicting an algorithm for monitoring a patient, according to embodiments of the present disclosure.
Figure 23:
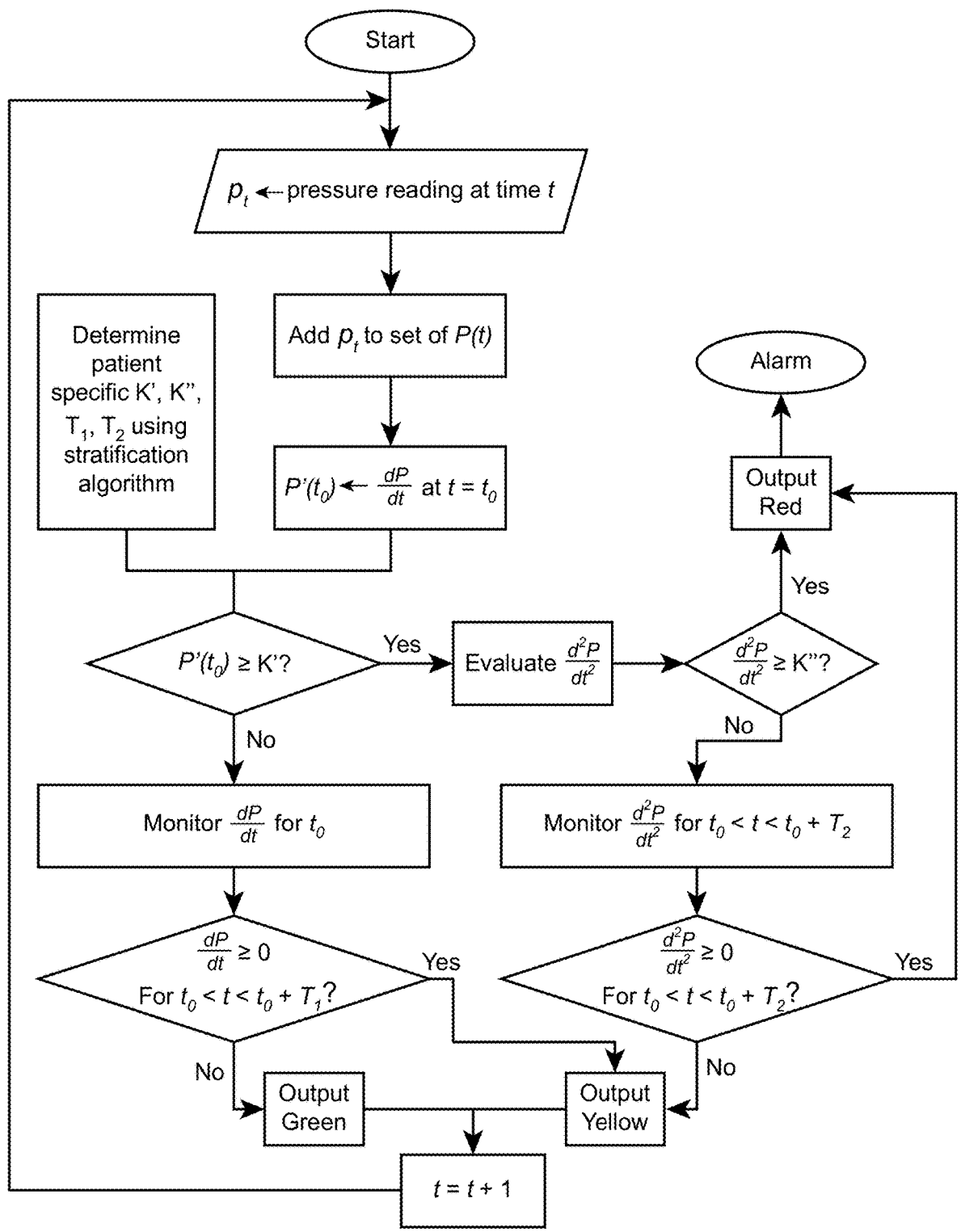
FIG. 23 is a flow chart depicting an algorithm for monitoring a patient, according to embodiments of the present disclosure.

In some cases, multiple threshold criteria may be used to analyze the pressure data. Thus, FIG. 22 shows a flow chart for determining whether multiple threshold criteria have been met by pressure data obtained from a patient, according to embodiments of the present disclosure. Risk variables may be obtained from the patient's medical records, as described above, and the patient-specific risk variables may be passed through a stratification algorithm to derive patient-specific threshold values:

κ' for the rate of change in the pressure;
κ" for the second derivative of pressure (as a function of time), i.e., the rate of pressure change;
$T_1$ for the time period during which the pressure increases; and
$T_2$ for the time period during which the rate of pressure change increases, using the patient's medical records as input to the stratification algorithm. A pressure reading may be obtained at a number of time points $t_1, t_2, \ldots t_n$, where n is an integer greater than 1, to generate a time series of pressure measurements $P(t)=(p_{t_1}, p_{t_2}, \ldots, p_{t_n})$. The analysis of the pressure data may include first determining if a first threshold criterion, associated with the threshold value κ', is met at an given time point. The first threshold criterion may be met if the first derivative of P(t):

$$\frac{dP(t)}{dt}$$

evaluated at $t=t_0$, where to may be the time of a contemporaneous pressure reading, is equal to or greater than κ', or the first threshold criterion may not be met if $$\frac{dP(t)}{dt}$$

evaluated at $t=t_0$, is less than κ'.

If the first threshold criterion is met, the pressure data may be analyzed with respect to a second threshold criterion, associated with the threshold value κ". The second threshold criterion may be met if the second derivative of P(t):

$$\frac{dP^2(t)}{dt^2}$$

evaluated at $t=t_0$ is equal to or greater than $\kappa''$, or the second threshold criterion may not be met if $$\frac{dP^2(t)}{dt^2}$$

evaluated at $t=t_0$ is less than $\kappa''$. If the second threshold criterion is met, an output may be generated, as described above, indicating to an individual, e.g., an individual monitoring the patient, that one or more threshold criteria have been sufficiently met.

If the first threshold criterion is not met, the pressure data may be analyzed with respect to a third threshold criterion, associated with the threshold value $T_1$, which may be a first monitoring time period. The third threshold criterion may be met if $$\frac{dP(t)}{dt}$$

is equal to or greater than 0 for the duration of the first monitoring time $T_1$ measured from $t_0$, or the third threshold criterion may not be met if $$\frac{dP(t)}{dt}$$

is less than 0 at some time point during the first monitoring time $T_1$. If the third threshold criterion is met, an output may be generated, as described above, indicating to an individual, e.g., an individual monitoring the patient, that one or more threshold criteria have been sufficiently met. If the third threshold criterion is not met, the analysis may proceed for the next pressure reading.

If the second threshold criterion is not met, the pressure data may be analyzed with respect to a fourth threshold criterion, associated with the threshold value $T_2$, which may be a second monitoring time period. The fourth threshold criterion may be met if $$\frac{d^2P(t)}{dt^2}$$

is equal to or greater than 0 for the duration of the second monitoring time $T_2$ measured from $t_0$, or the fourth threshold criterion may not be met if $$\frac{d^2P(t)}{dt^2}$$

is less than 0 at some time point during the second monitoring time $T_2$. If the fourth threshold criterion is met, an output may be generated, as described above, indicating to an individual, e.g., an individual monitoring the patient, that one or more threshold criteria have been sufficiently met. If the fourth threshold criterion is not met, the analysis may proceed for the next pressure reading.

In some embodiments, a tiered output may be generated to provide a more nuanced indication of the state of the patient. With respect to FIG. 23, another implementation of the present method may include the use of a tiered output such that the tier level of the output indicates the number, net number, and/or types of threshold criteria that have been met by the pressure data obtained from the patient. Such an embodiment of the present method may include obtaining risk variables from the patient's medical records, as described above, and the patient-specific risk variables may be passed through a stratification algorithm to derive patient-specific threshold values $\kappa'$; $\kappa''$; $T_1$; and $T_2$, as described above with respect to FIG. 22, using the patient's medical records as input to the stratification algorithm. A pressure reading may be obtained at a number of time points $t_1$, $t_2$, ... $t_n$, where n is an integer greater than 1, to generate a time series of pressure measurements $P(t)=(p_{t_1}, p_{t_2}, \ldots, p_{t_n})$. Then, the analysis of the pressure data may include determining if one or more of a first, second, third, and fourth threshold criteria, associated with the threshold values $\kappa'$, $\kappa''$, $T_1$, and $T_2$, respectively, are met by the pressure data, as described above with respect to FIG. 22. Depending on the particular threshold criterion that is met by the pressure data, a tiered output may be generated. The tiered output may include a high-tier output, e.g., red color-coded visual output, an intermediate-tier output, e.g., yellow color-coded visual output, or a low-tier output, e.g., a green color-coded visual output. The tiered output may be assigned according to the following rule shown in table 1.

TABLE 1

| Output tier | Criterion met? | | | | Net number of criteria met |
|---|---|---|---|---|---|
| | 1 | 2 | 3 | 4 | |
| High (e.g., red) | yes | yes | — | — | +2 |
| | yes | no | — | yes | +1 |
| Intermediate | yes | no | — | no | −1 |
| (e.g., yellow) | no | — | yes | — | 0 |
| Low (e.g., green) | no | — | no | — | −2 |

Upon meeting sufficient threshold criteria for the high-tier output, an alarm, e.g., an auditory, visual alarm, etc., may be generated, the alarm intended to inform an individual, e.g., an individual monitoring the patient, of the event. After meeting sufficient threshold criteria for the intermediate- or low-tier output, the analysis may proceed for the next pressure reading.

Figure 24:
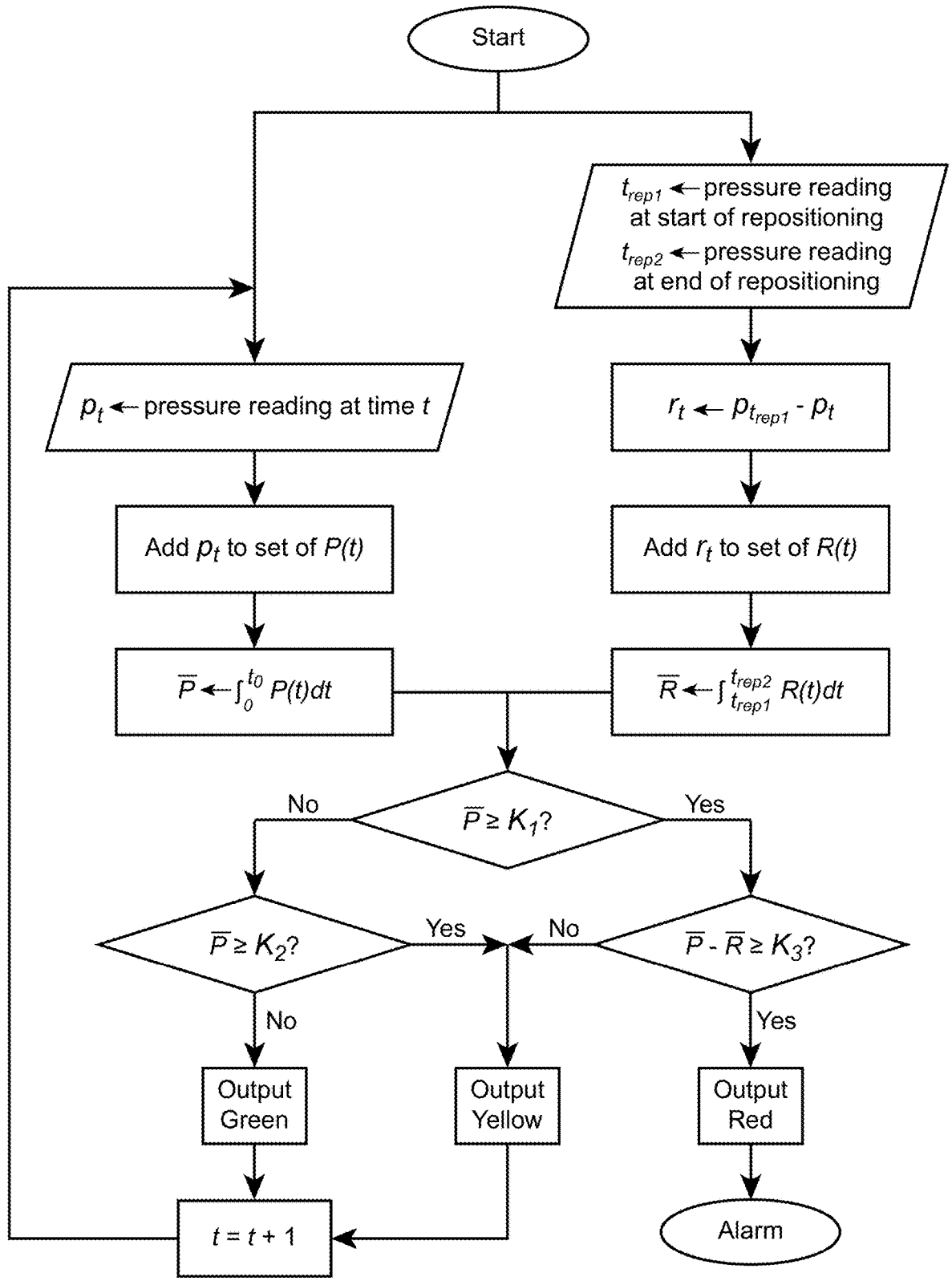
FIG. 24 is a flow chart depicting an algorithm for monitoring a patient, according to embodiments of the present disclosure.

In some cases, the method may take into account the effect that any prior intervention may have had on the amount of pressure applied to one or more body parts of the patient. FIG. 24 shows another flow chart for determining whether multiple threshold criteria have been met by pressure data obtained from a patient, according to embodiments of the present disclosure. The patient may have undergone a repositioning process, e.g., to relieve pressure applied to a pressure ulcer-prone body part that is being monitored by, e.g., a pressure-sensing device and system according to embodiments of the present disclosure. The start time of the repositioning may be $t_{rep1}$, and the repositioning may be completed at time $t_{rep2}$. The pressure reading from the pressure-sensing device at the start of the repositioning process may be $p_{t_{rep1}}$.

Risk variables may be obtained from the patient's medical records, as described above, and the patient-specific risk variables may be passed through a stratification algorithm to derive patient-specific threshold values:

$K_1$ for a first threshold for the integral, e.g., sum, of pressure over time;

$K_2$ for a second threshold for the integral, e.g., sum, of pressure over time; and $K_3$ for the difference between the integral, e.g., sum, of pressure over time and the total amount of pressure relieved by the repositioning of the patient, using the patient's medical records as input to the stratification algorithm. A pressure reading may be obtained at a number of time points $t_1, t_2, \ldots t_n$, where n is an integer greater than 1, to generate a time series of pressure measurements $P(t)=(p_{t_1}, p_{t_2}, \ldots, p_{t_n})$. The analysis of the pressure data may include determining if a first threshold criterion, associated with the threshold value $K_1$, is met at any given time point. The first threshold criterion may be met if the time integral of the pressure measurements P(t), from an arbitrary time point set to 0, which may coincide with the time at which monitoring of the patient started, to a current time point $t_0$ (e.g., the time of the most recent pressure reading): $\int_0^{t_0} P(t)dt$ is equal to or greater than $K_1$, and may not be met if $\int_0^{t_0} P(t)dt$ is less than $K_1$.

If the first threshold criterion is met, the pressure data may be analyzed with respect to a third threshold criterion, associated with the threshold value $K_3$. The third threshold criterion may be met if the difference between $\int_0^{t_0} P(t)dt$ and the time-integrated sum of the pressure relieved by the repositioning: $\int_{t_{rep1}}^{t_{rep2}} (p_{t_{rep1}} - R(t))$, where R(t) is a subset of P(t) where $t_{rep1} \leq t \leq t_{rep2}$, is equal to or greater than $K_3$, and may not be met if this difference is less than $K_3$.

If the first threshold criterion is not met, the pressure data may be analyzed with respect to a second threshold criterion, associated with the threshold value $K_2$. The second threshold criterion may be met if $\int_0^{t_0} P(t)dt$ is equal to or greater than $K_2$, and may not be met if $\int_0^{t_0} P(t)dt$ is less than $K_2$.

Depending on the particular threshold criterion that is met by the pressure data, a tiered output may be generated, as described above. The tiered output may be assigned according to the following rule shown in table 2.

TABLE 2

| Output tier | Criterion met? | | | Net number of criteria met |
|---|---|---|---|---|
| | 1 | 2 | 3 | |
| High (e.g., red) | yes | — | yes | +2 |
| Intermediate (e.g., yellow) | yes | — | no | 0 |
| | no | yes | — | 0 |
| Low (e.g., green) | no | no | — | −2 |

Upon meeting sufficient threshold criteria for the high-tier output, an alarm, e.g., an auditory, visual alarm, etc., may be generated, the alarm intended to inform an individual, e.g., an individual monitoring the patient, of the event. After meeting sufficient threshold criteria for the intermediate- or low-tier output, the analysis may proceed for the next pressure reading.

In some cases, the present method includes providing one or more instructions, intended for an individual, e.g., an individual monitoring the patient, to take an action (e.g., whether, how and/or when to reposition the patient; provide another level of intervention, e.g., medical intervention; seek medical attention; etc.) based on the pressure data obtained from the patient and the analysis of the pressure data using any suitable algorithm. In some embodiments, the method may include analyzing pressure data obtained from different part of the patient's body and determining if any or all of the pressure data meets one or more threshold criteria using a suitable algorithm as described herein.

Figure 25:
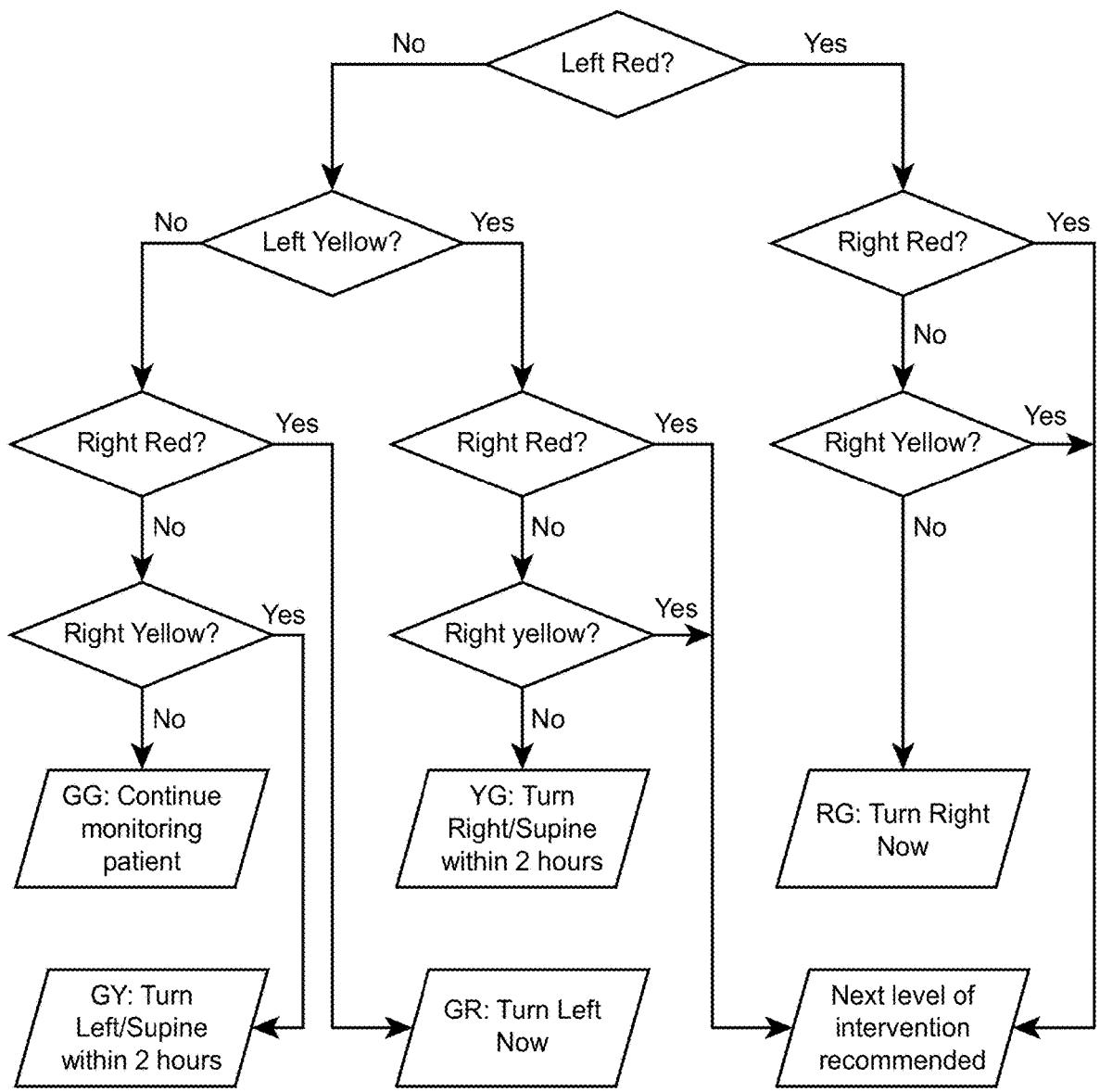
FIG. 25 is a decision tree depicting a method for monitoring a patient, according to embodiments of the present disclosure.

FIG. 25 shows an embodiment of the present method where pressure data from the left and right sides of a patient's body is analyzed to provide instructions for if, how and when to reposition the patient from lying on one side of the body to the other, or to provide a different level of intervention, based on an analysis of the pressure data. The analysis may include determining the level of the tiered-output generated upon analysis of data from the left side and right sides. Thus, if both sides of the body show an output that is intermediate or higher (e.g., yellow or red), then the user may be provided with an instruction that intervention beyond a simple repositioning is required now. If one side of the body shows a high-tier output and the other side shows a low-tier output, then the user may be provided with an instruction to turn the patient now such that pressure is applied to the side of the body showed the low-tiered output and pressure is relieved from the side that showed the high-tier output. If one side of the body shows an intermediate-tier output and the other side shows a low-tier output, then the user may be provided with an instruction to turn the patient within a predetermined time period (e.g., 2 hours) such that pressure is applied to the side of the body showed the low-tiered output and pressure is relieved from the side that showed the intermediate-tier output. If both sides of the body show a low-tier output, no specific instruction may be generated, or the user may be provided with an instruction to continue monitoring the patient without the need for any intervention now or within a predetermined time period based on the currently available pressure data.

In certain embodiments, the data obtained from the pressure-sensing device includes a contemporaneous pressure measurement, where the signal generated in response to force applied to the body part monitored by the pressure-sensing device is obtained continuously as a stream of data. The analyzing may in such cases include analyzing the stream of data as they are obtained from the pressure-sensing device.

The patient may be monitored for any convenient length of time. In some embodiments, data is obtained continuously from the patient for 30 minutes or more, e.g., 1 hour or more, 2 hours or more, 5 hours or more, 10 hours or more, 24 hours or more, 1 day or more, 2 days or more, including 5 days or more, and is obtained continuously from the patient for 20 years or less, e.g., 10 years or less, 5 years or less, 1 year or less, 6 months or less, 3 months or less, 1 month or less, including 2 weeks or less. In some embodiments, data is obtained continuously from the patient for 30 minutes to 20 years, e.g., 1 hour to 10 years, 2 hours to 5 years, 2 hours to 1 year, 5 hours to 6 months, 5 hours to 3 months, including 10 hours to 1 month.

The data may be obtained at a predetermined interval or frequency, which may be any suitable interval or frequency, for the pressure-sensing device as a whole, or for the individual pressure-sensitive elements in a pressure-sensing device. In some embodiments, the data is obtained at a frequency of 0.01 Hz or higher, e.g., 0.05 Hz or higher, 0.1 Hz or higher, 0.5 Hz or higher, 1 Hz or higher, 2 Hz or higher, 5 Hz or higher, 10 Hz or higher, 50 Hz or higher, 100 Hz or higher, including 200 Hz or higher, and is obtained at a frequency of 1,000 Hz or lower, 500 Hz or lower, 300 Hz or lower, 150 Hz or lower, 100 HZ or lower, 30 Hz or lower, including 10 Hz or lower. In some cases, the data is obtained at a frequency in the range of 0.01 to 1,000 Hz, e.g., 0.05 to 500 Hz, 0.1 to 300 Hz, 0.5 Hz to 150 Hz, including 1 to 100 Hz. In some embodiments, the data is obtained at an average interval of 1 ms or more, e.g., 5 ms or more, 10 ms or more, 100 ms or more, 500 ms or more, 1 sec or more, 5 sec or more, 10 sec or more, including 60 sec or more, and is obtained at an average interval of 600 sec or less, e.g., 300 sec or less, 120 sec or less, 60 sec or less, 30 sec or less, 10 sec or less, including 1 sec or less. In some embodiments, the data is obtained at an average interval in the range of 1 ms to 600 sec, e.g., 5 ms to 300 sec, 10 ms to 120 sec, 100 ms to 60 sec, including 500 ms to 30 sec.

The output generated based on the analysis may be any suitable output, and may indicate whether one or more threshold criteria are met by the pressure data, how many (total or net number) of the one or more threshold criteria are met by the pressure data, and/or which of the one or more threshold criteria are met by the pressure data. In some cases, the output is a visual output, auditory output, a tactile output, etc. A visual output may be any suitable visual output, and may convey the results of the analysis by letters, symbols, color, spatial pattern, temporal pattern, intensity, etc. An auditory output may be any suitable auditory output, and may convey the results of the analysis by voice, intensity, temporal pattern, pitch, etc. A tactile output may be any suitable tactile output, and may convey the results of the analysis by vibration, temperature, temporal pattern, spatial pattern, magnitude, etc.

A multi-tiered output may include any number of tiers, as necessary. In some cases, each threshold criterion is associated with one or two tiers of outputs. In some cases, each tier of output is intended to be conveyed to an individual, e.g., an individual monitoring a patient, by a corresponding output, e.g., a visual output, auditory output, tactile output, etc. The plurality of tiers may include 2 or more, e.g., 3 or more, 4 or more, 5 or more, 6 or more, 8 or more, including 10 or more tiers of outputs, and may include 50 or fewer, e.g., 40 or fewer, 30 or fewer, 20 or fewer, including 10 or fewer tiers. In some cases, the plurality of tiers may include 2 to 50 tiers, e.g., 2 to 40 tiers, 2 to 30 tiers, 3 to 20 tiers, including 3 to 10 tiers.

The threshold criteria may be any suitable threshold criteria. In some cases, one or more threshold criteria are standardized criteria applied to all or a group of patients, grouped based on one or more suitable factors, e.g., age, ethnicity, sex, disease diagnosis, etc. In some cases, one or more threshold criteria are patient-specific threshold criteria, as described above. Thus, in certain embodiments, a method of the present disclosure may include using a stratification algorithm to derive one or more patient-specific threshold criteria. Patient data (e.g., patient medical records) may be used as an input to the stratification algorithm to derive the one or more patient-specific threshold criteria.

The stratification algorithm for deriving patient-specific threshold criteria may be any suitable algorithm, and may be generated by, e.g., analyzing a database of medical records from a number of patients. The analysis may include, in some cases, statistical comparison and/or machine learning-based analysis of a database of patients. The database may include medical history of patients, and/or longitudinal collection of medical data of patients. The patients may or may not have developed a pressure ulcer. Medical data for analysis may include, without limitation, vital signs (body temperature, pulse rate, respiration rate, blood pressure, etc.), laboratory-analyzed values (e.g., levels and/or presence of electrolytes, nutritional markers, inflammatory markers, chronic disease markers), demographic information (e.g., age, sex, ethnicity, race), history of incontinence, mobility status, medication history, neurologic status, list of active comorbid diagnoses, Braden Scale score, and literature-validated intensive care unit (ICU) disease severity scores.

In some embodiments, the present method may include obtaining data from multiple pressure-sensing devices. Data may be obtained from any suitable number of pressure-sensing devices. In some cases, data is obtained from one or more, e.g., 2 or more, 3 or more, 4 or more, 6 or more, 8 or more, 12 or more, including 15 or more, and is obtained from 50 or fewer, e.g., 40 or fewer, 30 or fewer, 20 or fewer, 10 or fewer, including 6 or fewer pressure-sensing devices. In some embodiments, data is obtained from 1 to 50, e.g., 1 to 30, 1 to 10, including 2 to 6 pressure-sensing devices.

In some cases, the present method further includes repositioning the patient based on the output, as described herein. Repositioning the patient may be achieved in any suitable method. In some cases, the repositioning is done by an individual monitoring the patient, or any other care taker of the patient (e.g., physician, nurse practitioner, social worker, family member, etc.). In some cases, the repositioning is achieved by a repositioning device configured to alter a support surface, e.g., a bed, supporting the patient and to shift the distribution of the patient's weight on the support surface. Thus, in such cases, the output of the present method may be provided to the repositioning device as an instruction controlling the repositioning device.

In some cases, the present method further includes providing instructions intended for an individual, e.g., an individual monitoring a patient. The instructions may contain any suitable messages that inform the individual of one or more recommended courses of action with respect to the patient being monitored. The instructions may provide one or more recommended courses of action that will reduce the risk for the patient to develop a pressure ulcer, or prevent an increase in the risk for the patient to develop a pressure ulcer. In some cases, the instructions contain a recommendation to reposition the patient from a current, first position to a second position, such that the pressure currently applied to one or more body parts of the patient is relieved. In some cases, the recommendation is to continue monitoring without any intervention. In some cases, the recommendation is to seek and/or provide an alternative level of intervention other than repositioning the patient. The alternative level of intervention may be any suitable intervention that may reduce the risk for the patient to develop a pressure ulcer, or prevent an increase in the risk for the patient to develop a pressure ulcer, and that may not be possible by repositioning alone. In some cases, the alternative level of intervention is recommended when repositioning alone is not expected to reduce the risk for the patient developing a pressure ulcer, or prevent an increase in the risk for the patient to develop a pressure ulcer.

The instructions may recommend an action to be taken in any suitable time frame. In some cases, the instructions include recommendations to take action immediately. In some cases, the instructions include recommendations to take action within a certain time period, such as in 10 min or more, e.g., 20 min or more, 30 min or more, 45 min or more, 1 hr or more, 1.5 hrs or more, 2 hrs or more and to take action within 12 hrs or less, e.g., 8 hrs or less, 4 hrs or less, 3 hrs or less, including 2 hrs or less.

The instructions may be provided in any convenient form. The instructions may be provided in digital format, e.g., database entry, screen display, text message, electronic mail, etc.; a tangible medium, e.g., paper; an auditory message, e.g., a vocal instruction; etc.

In some cases, the method further includes attaching one or more pressure-sensing devices to a patient before start of monitoring. The pressure-sensing devices may be attached to any suitable body part of the patient, as described above.

The pressure-sensing devices may be attached by any convenient method. In certain embodiments, the pressure-sensing devices are attached to the patient in a similar manner to a wound dressing, as described in, e.g., U.S. Pat. Nos. 5,153,040; 5,540,922; 5,755,681; 7,094,944; 8,497,407 and US20040126413, each of which is incorporated herein by reference. In some cases, the pressure-sensing devices are strapped onto the patient using bandage, e.g., a gauze. In some embodiments, the pressure-sensing devices include an adhesive layer containing, e.g., a self-adhesive, which may be used to attach the pressure-sensing devices to the body part.

Kits

Also provided is a kit that finds use in the system of the present disclosure, and in performing the method of the present disclosure. The present kit may include a) one or more pressure-sensing devices, each containing a pressure-sensitive region, as described above; and b) a controller that includes a communication unit configured to transmit data containing pressure measurements based on the force sensed by the one or more pressure-sensing devices. In some cases, the pressure-sensing device includes a multilayered sensing unit that contains a pressure-sensing layer containing an array of interconnected pressure-sensitive elements, wherein each pressure-sensitive element of the array is configured to sense force applied to the body part and generate a signal representative of a magnitude of the force; and an adhesive layer configured to attach the pressure-sensing device to the body part.

The present kit in some cases further includes a non-transient computer-readable memory comprising instructions that cause a computational unit to i) obtain the data transmitted by the one or more pressure-sensing devices; and ii) analyze the obtained data using one or more threshold criteria, each of the one or more threshold criteria including a threshold value, to determine whether the one or more threshold criteria have been met, as described herein.

The present kit may include any other suitable component for monitoring a patient, as described herein. In some cases, the present kit includes instructions for using the present kit. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™, etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

EXAMPLES

Example 1: Accurate Measurement of Pressure Data Using Pressure Sensors

The pressure-monitoring system was calibrated using standard weights. The system was tested in a controlled setting with randomly placed standard weights. The accuracy of the system was determined quantitatively for over 4 days.

Example 2: Continuous Monitoring of Pressure on Subjects

Figure 26:
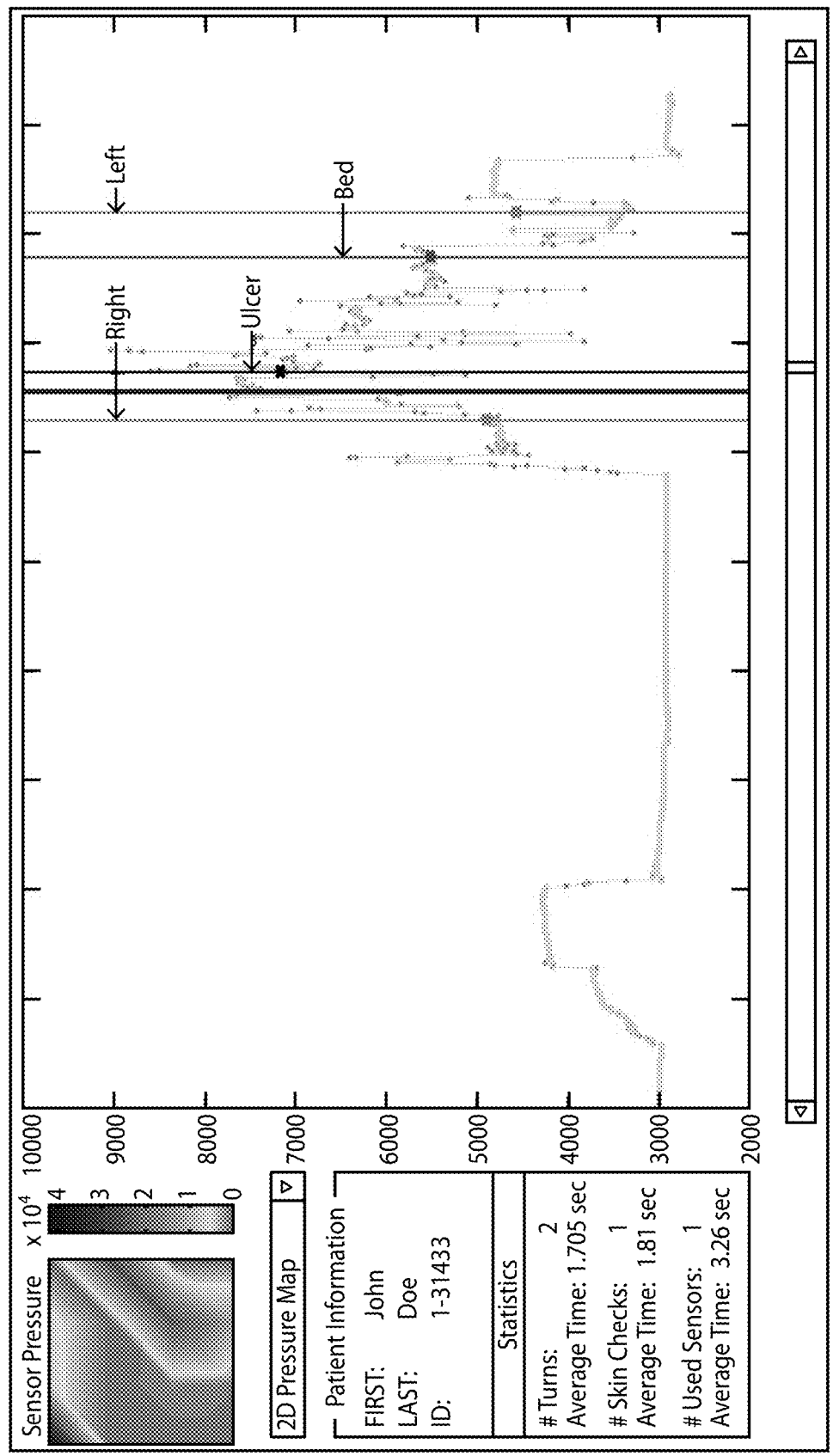
FIG. 26 is graph showing time course of pressure measurements obtained from a pressure-sensing device on a patient's body part, according to embodiments of the present disclosure. The measured values are in arbitrary voltage units.

Sensors were attached to the external surface of a Mepilex® sacral wound dressing, connected through the tab to an electronics board placed within plastic casings, and placed on the lower back using standard Mepilex® placement guidelines on multiple subjects, and pressure-over-time data were collected continuously over 14 hours at a rate of one pressure reading per pressure cell per second. Qualitatively, these subject tests indicated the accuracy of our system in measuring pressure through various identifiable events, such as the subject sitting up, lying down, leaving the bed, returning to bed, or moving to a left/right/supine position (sample data averaging pressure, collected at a rate of ten samples per pressure cell per second over the duration of six hours, over 16 cells on a pressure sensor attached to a Mepliex® wound dressing placed on the lower back of one subject, is shown in FIG. 26, with the flat section corresponding to the subject periodically adjusting himself in a standing position, and the more actively changing data portion corresponding to the subject in a seated position. The marked times denoting ulcer and patient repositioning were placed to test UI elements of the software and do not correspond to medical events.).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Example 3

Method and Materials:

Pressure sensitive wound dressing: The tested sensor patch consisted of a 4×4 square grid of pressure sensing variable resistor cells (Uneotech) sensitive from 0.01-300 PSI placed between a Mepilex Border Sacrum (Mölnlycke Health Care) wound dressing and Tegaderm (3M) transparent film. Wires from the sensing grid were routed through a 30 cm flexible flat cable at the side of the sensor that terminated with 8 conductors. These 8 conductors plug in to the female port in the electronics box.

Electronics box: The electronics box was a 3D printed plastic box that contained a printed circuit board with microcontroller, Bluetooth chip, circuit components to receive pressure data from the sensor, and a replaceable coin cell battery. The 3D printed plastic casing was designed to be pinned to the front of a patient's gown after a pressure sensitive wound dressing is plugged into the box.

Clinical application: An iPad application enabled interaction with the nurses and data collection. The application connected to the electronics box when a patient was enrolled, received and stored pressure data, and allowed nurses to annotate when patients were turned or a new sensor was applied.

Data collection procedure: A patient is consented and enrolled in the study. The patient's skin is observed for lesions, baseline documentation is performed, and the pressure sensitive wound dressing is placed on the sacrum of the patient following standard Mepilex application procedures.

The end of the flexible flat cable is plugged into the electronics box and a coin cell battery is placed into the electronics box. The clinical application is selected on the iPad and the patient's study number is entered into the application. Once the patient's number is entered into the application, the iPad connects to the electronics box and commences data collection. The PCB scans across the pressure sensor and measures the change in resistance at each cell in order to determine pressure. 1 sample is collected from the full sensor every second and transmitted to the clinical application, which stores the pressure data for each patient.

Data annotation: When patients are repositioned, the nurse notes the repositioning event on the clinical application and specifies which side the patient was turned to (left, right, or supine). This timestamps the event and links the event to the pressure measured at that time, through which the change in pressure correlated with the specific repositioning event can be determined. Data collection continues throughout a patient's stay in the ICU until the patient is discharged from the ICU or develops a skin condition.

Test Subjects:

Subject 1 (healthy): Subject 1 was observed on a standard hospital bed for <1 hour, during which he changed position voluntarily.

Subject 2 (healthy): Subject 2 was observed sitting on a chair for 4 hours with intermittent periods during which he stood up and briefly walked before sitting down again.

Patients 1-5 were observed in an Intensive Care Unit (ICU) at UCSF. All patients required manual turning by nurses/PCAs.

Results:

Sensor results were collected, averaged and provided in Table 3, below.

TABLE 3

Average and Maximum pressure observed on healthy subjects and high risk patients

| Test Subject | Observation | Average Pressure (mmHG) | Maximum Pressure (mmHg) |
| --- | --- | --- | --- |
| Subject 1 (Healthy) | Hospital Bed <1 hour | 12.56 mmHg | 32.05 mmHg |
| Subject 2 (Healthy) | Chair 4 hours | 46.01 mmHg | 121.95 mmHg |
| Patient 1 | ICU 9 days | 20.06 mmHg | 142.17 mmHg |
| Patient 2 | ICU 1 days | 23.18 mmHg | 120.46 mmHg |
| Patient 3 | ICU 2 days | 28.40 mmHg | 143.07 mmHg |
| Patient 4 | ICU 4 days | 20.32 mmHg | 141.96 mmHg |
| Patient 5 | ICU 2 days | 24.10 mmHg | 142.53 mmHg |

Subject 1's average pressure was lowest measured (12.56 mmHg). The subject was capable of moving himself and prevented the maximum pressure experienced from exceeding 32.05 mmHg which may represent a lower bound on pressure at which discomfort is experienced.

Subject 2's average pressure was highest measured subjects (46.01 mmHg). The variation in pressure experienced by this subject was also greatest out of all the tested subjects (i.e. this subject spent the longest time at higher pressures punctuated with periods of standing and negligible recorded pressure). This periodic offloading of pressure by a healthy subject may indicate that 46.01 mmHg may represent an upper bound for sustained pressure for healthy subjects.

Figure 27:
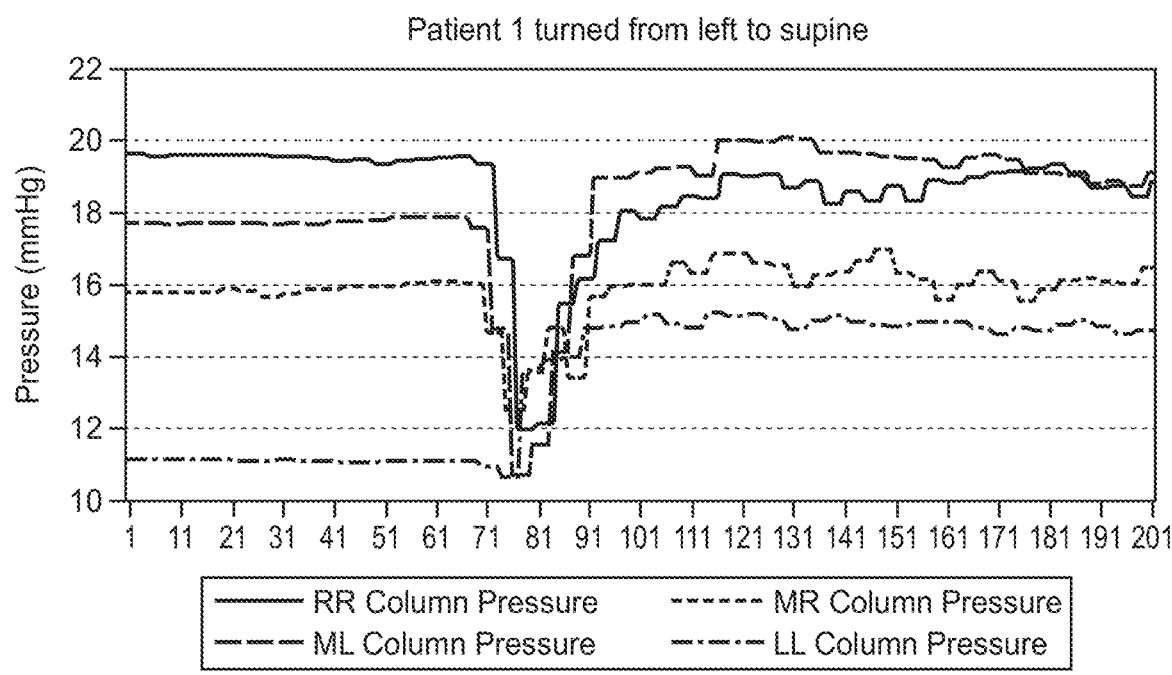
FIG. 27 is a graph showing average pressure by column as patient 1 is turned from left to supine.

For both healthy subjects and patients, average pressures tended to remain within 10-20 mmHg. FIG. 27 provides an illustrative example of the change in pressures generally observed when a patient is repositioned. Data from before and after a patient is turned from left to supine is shown in FIG. 27. During the patient's repositioning, the pressure on the right most side of the sensor increased from 10 mmHg to 15 mmHg, pressure on the left most side of the sensor fell from 20 mmHg to 18 mmHg, and pressure on the middle left side of the sensor increased from 18 mmHg to 20 mmHg.

Figure 28:
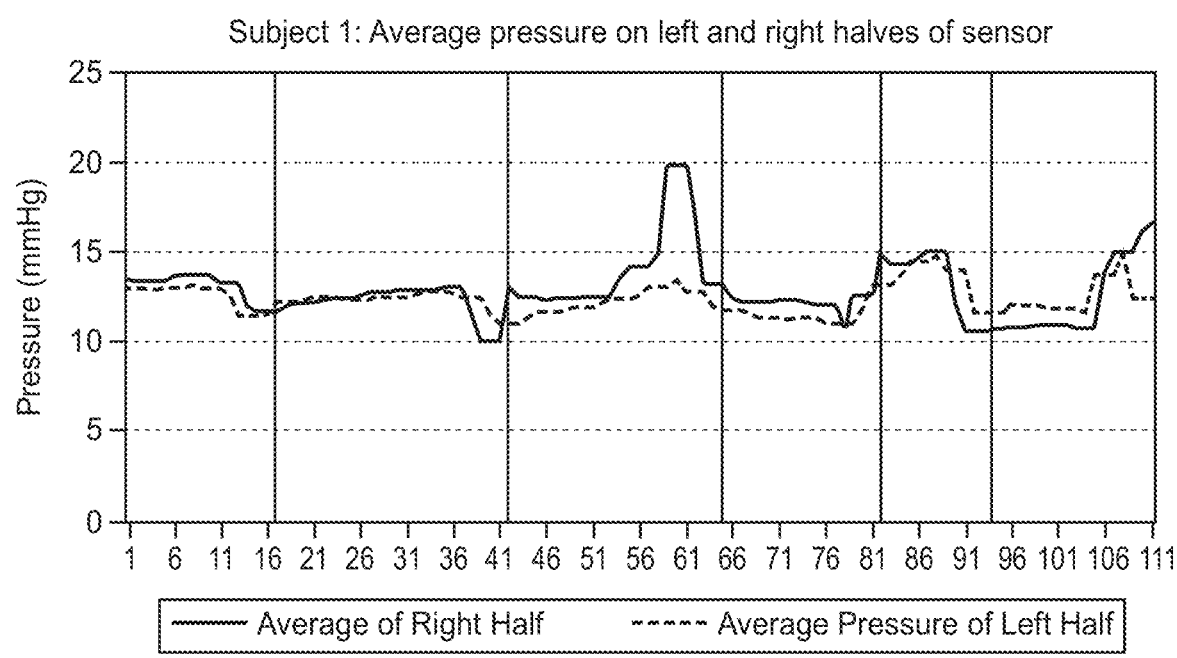
FIG. 28 is graph showing average pressure on each sensor half recorded on subject 1.

FIG. 28 provides an illustrative example of the change in pressures generally observed when a healthy subject is recumbent on a bed and is capable of adjusting his or her own position. The time period when the greatest pressure is observed (right half pressure is ~20 mmHg) is relatively short due to the subject being able to move himself.

What is claimed is:

1. A system for a user to monitoring a patient, comprising:
   a) one or more pressure-sensing devices, wherein each of the pressure-sensing devices comprises a pressure-sensitive region configured to:
      be overlaid on one of one or more pressure ulcer-prone body parts of a body of the patient;
      and
      sense force applied to the body and generates a signal representative of a magnitude of the force,
      and wherein each of the pressure-sensing devices is configured to generate data comprising two pressure measurements from different times based on the sensed force;
   b) a controller comprising a communication unit;
   a computational unit comprising:
      a processor; and
      a non-transient computer-readable memory comprising instructions that, when executed by the processor, causes the computational unit to:
      i) obtain the data transmitted by the one or more pressure-sensing devices;
      ii) processing the two pressure measurements from different times of the data to generate a processed pressure datum, wherein the processing comprises calculating a time-differential of the data: dP(t)/dt, where P(t) is a function comprising a temporal sequence of the pressure measurements value, $p_t$; and
      iii) determine whether the processed pressure datum meets a threshold value; and
   c) a user-interface unit comprising an output unit configured to display an output comprising:
   the data, or the processed pressure datum; and/or
   an indication of whether the threshold value is met by the data.

2. The system of claim 1, wherein each of the pressure-sensing devices comprises a multilayered sensing unit comprising:
   a pressure-sensing layer comprising an array of interconnected pressure-sensitive elements, wherein each pressure-sensitive element of the array is configured to sense the force applied to the body part and generate the signal representative of the magnitude of the force; and
   an adhesive layer configured to attach the pressure-sensing device to the body part.

3. The system of claim 2, wherein the pressure-sensing layer comprises a first conductive layer comprising a first substrate, a second conductive layer comprising a second substrate, and a piezoresistive layer comprising a pressure-sensitive polymer, wherein the piezoresistive layer is interposed between the first and second conductive layers.

4. The system of claim 3, wherein the pressure-sensitive elements each comprises a conductive element disposed in each of the first conductive layer and the second conductive layer, wherein the conductive elements are in contact with the piezoresistive layer.

5. The system of claim 3, wherein the pressure-sensitive polymer comprises a piezoresistive polymer.

6. The system of claim 2, wherein the array is a grid, comprising one or more rows and one or more columns of pressure-sensitive elements.

7. The system of claim 6, wherein a location within the grid of each of the pressure-sensitive elements is specified by a row number and a column number.

8. The system of claim 6, wherein the data comprises information about a location within the grid of the pressure-sensitive element from which the signal originated.

9. The system of claim 2, wherein each pressure-sensitive element is substantially circular.

10. The system of claim 2, wherein each pressure-sensitive element has an average diameter in the range of 0.1 to 5 cm.

11. The system of claim 2, wherein a distance between adjacent pressure sensitive elements is in the range of 0.5 to 10.0 cm.

12. The system of claim 1, wherein the processing comprises calculating a time-integral of the data: $\int_0^{t_0} P(t)dt$, wherein $t_0$ is the time of a current pressure measurement.

13. The system of claim 1, wherein the threshold value is a patient-specific threshold value based on patient-specific factors for pressure ulcer development.

14. The system of claim 1, wherein the output further comprises an indication of a risk of developing a pressure ulcer.

15. The system of claim 1, wherein the computation unit also determines whether the processed pressure datum meets a second threshold value, and the output is a tiered output comprising a plurality of tiers of output, wherein the tier of the output is based on whether the processed pressure datum meets the threshold value and whether the processed pressure datum meets the second threshold value.

16. The system of claim 1, wherein the processing comprises calculating a second-order time-differential of the data:

$$\frac{d^2 P_n(t)}{dt^2}$$

where P(t) is a function comprising a temporal sequence of the pressure measurements value, $p_t$.

17. The system of claim 1, wherein one or more patient-specific criteria are met, the output further comprises instructions to: continue monitoring the patient; turn the patient's body; turn the patient's body within a predetermined amount of time; provide a level of intervention other than repositioning the patient; and/or seek medical attention.

* * * * *